United States Patent
Bischoff et al.

(10) Patent No.: US 6,984,642 B1
(45) Date of Patent: Jan. 10, 2006

(54) SUBSTITUTED PHENYLCYCLOHEXANE CARBOXYLIC ACID AMIDES AND THEIR USE AS ADENOSINE UPTAKE INHIBITORS

(75) Inventors: Erwin Bischoff, Wuppertal (DE); Stephan Lensky, Kürten (DE); Stephan-Nicholas Müller, Wuppertal (DE); Holger Paulsen, Wuppertal (DE); Jörg Keldenich, Wuppertal (DE); Thomas Krahn, Hagen (DE); Joachim Schuhmacher, Wuppertal (DE); Jan Jänichen, Hamburg (DE); Wolfgang Thielemann, Wuppertal (DE); Henning Steinhagen, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/980,242

(22) PCT Filed: May 16, 2000

(86) PCT No.: PCT/EP00/04431

§ 371 (c)(1),
(2), (4) Date: Nov. 29, 2001

(87) PCT Pub. No.: WO00/73274

PCT Pub. Date: Dec. 7, 2000

(30) Foreign Application Priority Data

May 29, 1999 (DE) .......................................... 199 24 819

(51) Int. Cl.
*A61K 31/496* (2006.01)
*C07D 403/04* (2006.01)

(52) U.S. Cl. .................... 514/254.06; 544/370
(58) Field of Classification Search ............ 514/254.06; 544/370
See application file for complete search history.

(56) References Cited

U.S. PATENT DOCUMENTS 5,395,840 A * 3/1995 Müller et al. ............... 514/300

5,935,983 A * 8/1999 Müller-Gliemann et al. ..... 514/397

FOREIGN PATENT DOCUMENTS

| EP | 0611767 | * | 8/1994 |
| EP | 0582164 | * | 9/1994 |
| EP | 0725064 | * | 7/1996 |
| WO | 9712060 | * | 3/1997 |

OTHER PUBLICATIONS

Jacobsen, P., Schaumburg, K., Larsen, J.-J., and Krogssgaard-Larsen, P., "Syntheses of Some Aminopiperidinecarboxylic Acids Related to Nipecotic Acid", Acta Chemica Scandinavica, B35: 289–294 (1981).*

Strasser, R., Vogt, A., Schaper, W., "Myokardprotektion Durch Prakonditionierung. Experimentelle und Klinische Bedeutung", Kardiol., 85: 79–89 (1996).

Makarewicz, W., "Response of Purine Metabolism to Hypoxia and Ischemia", Purine and Pyrimidine Metabolism in Man, Plenum Press, New York, 1998, 351–357.

* cited by examiner

*Primary Examiner*—Joseph K. McKane
*Assistant Examiner*—Rebecca Anderson

(57) ABSTRACT

The present invention relates to substituted phenylcyclohexanecaboxamides of the formula (I), to processes for their preparation and to their use in medicaments, in particular for treating cardiovascular disorders.

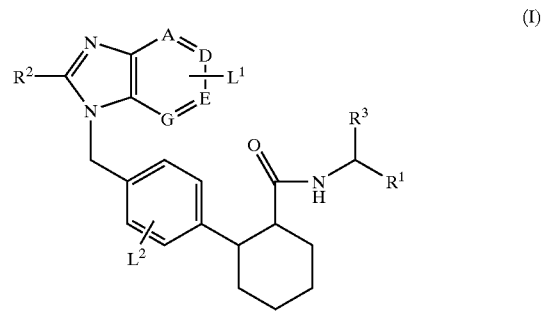

21 Claims, No Drawings

# SUBSTITUTED PHENYLCYCLOHEXANE CARBOXYLIC ACID AMIDES AND THEIR USE AS ADENOSINE UPTAKE INHIBITORS

The present invention relates to substituted phenylcyclohexanecarboxamides, to a process for their preparation and to their use in medicaments, in particular for treating cardiovascular disorders, for example for the acute and chronic treatment of ischaemic disorders.

Adenosine is an endogenic effector with cell-protective activity, in particular under cell-damaging conditions with limited oxygen supply, such as, for example, in ischaemia. Adenosine is a highly effective vasodilator. It increases ischaemic "preconditioning" (R. Strasser, A. Vogt, W. Scharper, Z. Kardiologie 85, 1996, 79–89) and can promote the growth of collateral vessels. It is released under hypoxic conditions, for example in the case of cardiac or peripheral occlusive diseases (W. Makarewicz "Purine and Pyrimidine Metabolism in Man", Plenum Press New York, 11, 1998, 351–357). Accordingly, adenosine protects against the effects of disorders caused by ischaemia, for example by increasing the coronary or peripheral circulation by vasodilation, by inhibiting platelet aggregation and by stimulating angiogenesis. Compared to systemically administered adenosine, the adenosine-uptake inhibitors have the advantage of selectivity for ischaemia. Systemically administered adenosine causes a strong general, but frequently undesired, lowering of the blood pressure. The adenosine-uptake inhibitor increases the effect of the adenosine which is formed locally owing to the ischaemia and thus only dilates the vessels in the ischaemic regions. Here, too, adenosine-uptake inhibitors increase the effects of adenosine and can be administered orally or intravenously for the prevention and therapy of ischaemic disorders, for example of coronary heart disease, of stable and unstable angina pectoris, of peripheral and arterial occlusive diseases, of thrombotic vascular occlusion, myocardial infarction and reperfusion damage. Moreover, owing to their potential to increase angiogenesis, they are particularly suitable for a permanent therapy of all occlusive diseases.

Adenosine-uptake inhibitors can also be used for potentiating the effect of nucleobase, nucleoside or nucleotide antimetabolites in the chemotherapeutical treatment of cancer and in antiviral (for example HIV) chemotherapy.

EP-A0 611 767 and EP-A-725 064 disclose phenylcyclohexylcarboxamides which can be used for the treatment of atherosclerosis or restenosis.

The present invention relates to compounds of the general formula (I)

in which
A, D, E and G are identical or different and represent CH groups or nitrogen atoms,
$L^1$ and $L^2$ are identical or different and independently of one another each represents one or more radicals selected from the group consisting of hydrogen, halogen, hydroxyl, carbxyl, cyano, nitro, trifluoromethyl, trifluoromethoxy, $(C_1-C_4)$-alkyl, $(C_1-C_6)$-alkoxy or $(C_1-C_6)$-alkoxycarbonyl,
$R^1$ represents the $CH_2$—OH group, or
represents a radical of the formula CO—NR $R^5$,
in which
$R^4$ and $R^5$ are identical or different and each represents hydrogen or $(C_1-C_6)$-alkyl,
$R^2$ represents $(C_3-C_8)$-cycloalkyl,
represents $(C_1-C_8)$-alkyl which is optionally interrupted by an oxygen or sulphur atom or by a radical $NR^6$
represents a 4- to 8-membered saturated heterocycle which is attached to the imidazole ring via a nitrogen atom and which optionally contains a further oxygen or sulphur atom, or
represents a 4- to 8-membered saturated heterocycle which contains a radical of the formula $NR^7$ and optionally additionally one nitrogen, oxygen or sulphur atom,
where $(C_3-C_8)$cycloalkyl, $(C_1-C_8)$alkyl which is optionally interrupted by an oxygen or sulphur atom, the 4- to 8-membered saturated heterocycle which is attached to the imidazole ring via a nitrogen atom and which optionally contains a further oxygen or sulphur atom and optionally $(C_1-C_8)$-alkyl which is interrupted by a radical $NR^6$ and optionally the 4- to 8-membered saturated heterocycle which contains a radical of the formula $NR^7$ and optionally additionally one nitrogen, oxygen or sulphur atom are substituted by one to three hydroxyl groups and/or by a radical of the formula —$NR^8R^9$
in which
$R^6$ and $R^7$ are identical or different and each represents hydrogen, $(C_1-C_4)$ alkyl, hydroxy-$(C_1-C_6)$-alkyl or $(C_3-C_7)$Cycloalkyl,
$R^8$ and $R^9$ are identical or different and each represents hydrogen, $(C_1-C_6)$ alkyl or $(C_3-C_7)$-cycloalkyl,
or
$R^8$ and $R^9$ together with the nitrogen atom form a 4- to 8-membered saturated heterocycle which may optionally additionally contain one oxygen or sulphur atom or a radical of the formula $NR^{10}$,
in which
$R^{10}$ represents hydrogen, $(C_1-C_6)$alkyl or $(C_3-C_7)$-cycloalkyl,
and
$R^3$ represents a phenyl, naphthyl, pyrimidinyl, pyridyl, furyl or thienyl ring, where the rings are optionally mono- or polysubstituted by radicals selected from the group consisting of halogen, hydroxyl, carboxyl, cyano, nitro, trifluoromethyl, trifluoromethoxy, $(C_1-C_6)$-alkyl, $(C_1-C_6)$alkoxy and $(C_1-C_6)$-alkoxycarbonyl,
and their enantiomers and diastereomers and their respective salts, hydrates and, if appropriate, their prodrugs.

Among these, preference is given to compounds of the general formula (I) having the stereochemistry of the general formula (Ia) below

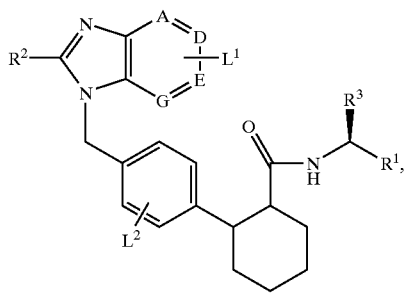

(Ia)

where the substituents $R^1$, $R^2$, $R^3$, $L^1$ and $L^2$ and the radicals A, D, E and G are as defined above.

Physiologically acceptable salts of the compounds according to the invention can be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Depending on the substitution pattern, the compounds according to the invention can exist in stereoisomeric forms which either are like image and mirror image (enantiomers) or are not like image and mirror image (diastereomers). The invention relates both to the enantiomers or diasteromers and to their respective mixtures. The racemic forms, like the diastereomers, can be separated in a known manner into the stereoisomerically uniform components.

According to the invention "hydrates" refer to those forms of the compounds of the above general formula (I) which, in the solid or liquid state, form a molecular compound (solvate) by hydration with water. In the hydrates the water molecules are added via secondary valence bonds effected by intermolecular forces—in particular hydrogen bridge bonds. Solid hydrates contain water in the form of so-called water of crystallization in stoichiometric ratios, although the bonding states of the water molecules do not necessarily have to be the same. Examples of hydrates are sesquihydrates, monohydrates, dihydrates or trihydrates. Possible hydrates can also be those of salts of the compounds according to the invention.

According to the invention, "prodrugs" are forms of the compounds of the general formula (I) or (Ia) above, which for their part can be biologically active or inactive, but which can be converted into the corresponding biologically active form (for example metabolically, solvolytically or in another way).

Examples of such "prodrugs" are, for example in the case that the above radical $R^2$ represents $(C_3-C_8)$-cycloalkyl, $(C_1-C_8)$-alkyl or a 4- to 8-membered saturated heterocycle, in each case substituted by one or more hydroxyl groups, compounds which can generate this/these hydroxyl group(s) metabolically, solvolytically or in another manner, for example esters, in particular amino acid esters (for example glycine esters, β-alanine esters, N-aminoethylglycine esters, etc.), phosphates, acetals, semiacetals, glucuronates, and the like.

$(C_1C_8)$-alkyl, $(C_1-C_6)$-alkyl etc., represent a straight-chain or branched alkyl radical having 1 to 8 or 1 to 6 carbon atoms. Examples which may be mentioned are: methyl, ethyl, n-propyl, isopropyl, tert-butyl, n-pentyl and n-hexyl. Preference is given to a straight-chain or branched alkyl radical having 1 to 4 carbon atoms $(C_1-C_4)$. Particular preference is given to a straight-chain or branched alkyl radical having 1 to 3 carbon atoms $(C_1-C_3)$.

$(C_1-C_8)$-alkyl, $(C_1-C_8)$-alkyl etc., which is interrupted by an oxygen or sulphur atom and which is substituted by one to three hydroxyl groups and/or by a radical of the formula —$NR^8R^9$ represent, for example, 1,3-dihydroxy-prop-2-oxy-methyl, 2-hydroxy-ethoxy-methyl, 2-hydroxy-prop-1-oxy-methyl, 3-hydroxy-prop-1-oxy-methyl, morpholin-4-yl-methyl, piperidin-1-yl-methyl, 2-amino-ethyl, 2-dimethylamino-ethyl or diethylamino-methyl.

$(C_1-C_8)$-alkyl, $(C_1-C_6)$-alkyl etc., which is interrupted by a radical $NR^6$ and which is optionally substituted by one to three hydroxyl groups and/or by a radical of the formula —$NR^8R^9$ represent, for example, N-(2-hydroxy-ethyl)-aminomethyl, N-(2-hydroxyethyl)-N-methyl-aminomethyl or N,N-bis-(2-hydroxy-ethyl)-aminomethyl.

Hydroxy-$(C_1-C_6)$-alkyl or hydroxy-$(C_1-C_4)$alkyl represents a straight-chain or branched alkyl radical having 1 to 6 or 1 to 4 carbon atoms. Examples which may be mentioned are: hydroxymethyl, 2-hydroxy-ethyl, 2-hydroxy-prop-1-yl, 3-hydroxy-prop-1-yl, 3-hydroxy-prop-2-yl, 2-hydroxy-but-1-yl, 5-hydroxy-pent-1-yl and 6-hydroxy-hex-1-yl. Preference is given to 2-hydroxy-ethyl.

$(C_1-C_6)$-Alkoxy represents a straight-chain or branched alkoxy radical having 1 to 6 carbon atoms. Examples which may be mentioned are: methoxy, ethoxy, n-propoxy, isopropoxy, tert-butoxy, n-pentoxy and n-hexoxy. Preference is given to a straight-chain or branched alkoxy radical having 1 to 4 carbon atoms $(C_1-C_4)$. Particular preference is given to a straight-chain or branched alkoxy radical having 1 to 3 carbon atoms $(C_1-C_3)$.

$(C_1-C_6)$-Alkoxycarbonyl represents a straight-chain or branched alkoxycarbonyl radical having 1 to 6 carbon atoms. Examples which may be mentioned are: methoxycarbonyl, ethoxycarbonyl, n-propoxycarbonyl, isopropoxycarbonyl and tert-butoxycarbonyl. Preference is given to a straight-chain or branched alkoxycarbonyl radical having 1 to 4 carbon atoms $(C_1-C_4)$. Particular preference is given to a straight-chain or branched alkoxycarbonyl radical having 1 to 3 carbon atoms $(C_1-C_3)$.

$(C_3-C_8)$Cycloalkyl, $(C_3-C_7)$-cycloalkyl etc., represent, in the context of the invention, cyclopropyl, cyclobutyl, cyclopentyl, cyclohexyl, cycloheptyl or cyclooctyl. Cyclopropyl, cyclopentyl and cyclohexyl may be mentioned as being preferred.

Halogen in the context of the invention generally represents fluorine, chlorine, bromine and iodine. Preference is given to fluorine, chlorine and bromine. Particular preference is given to fluorine and chlorine.

In the context of the invention, a 4- to 8-membered (preferably 5- to 7-membered) saturated heterocycle which is attached via a nitrogen atom and which optionally contains a further oxygen or sulphur atom represents, for example, pyrrolidin-1-yl, piperidin-1-yl, morpholin-4-yl, thiomorpholin-4-yl or 1H-hexahydroazepin-1-yl.

In the context of the invention, a 4 to 8-membered (preferably 5- to 7-membered) saturated heterocycle which contains a radical of the formula $NR^7$ and optionally additionally one nitrogen, oxygen or sulphur atom represents, for example, pyrrolidin-2-yl, 1-methylpyrrolidin-2-yl, pyrrolidin-3-yl, pyrazolidinl-yl, piperidin-2-yl, 1-isopropyl-piperidin-3-yl, morpholin-2-yl, 4-cyclohexyl-piperazin-1-yl, thiomorpholin-3-yl, 1-ethyl-1H-hexahydroazepin-3-yl or 4-methyl-1H-hexahydro-1,4 diazepin-1-yl. This heterocycle can be attached to the imidazole ring via a ring carbon atom or a ring nitrogen atom.

The compounds according to the invention can be present in eight different configurations, and preference is given to the four different configurations (A) to (D) below:

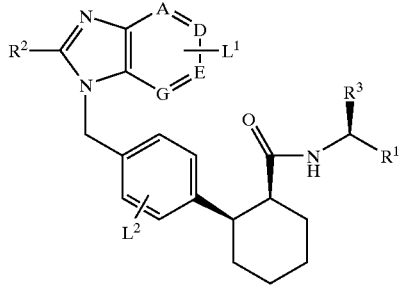
(A)

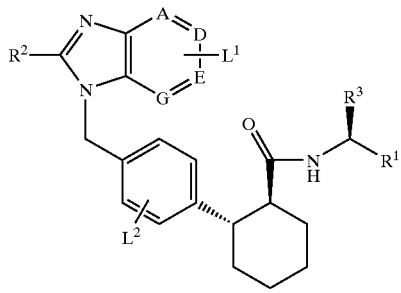
(B)

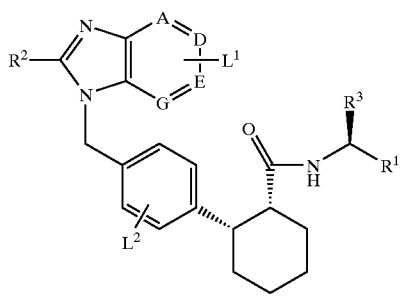
(C)

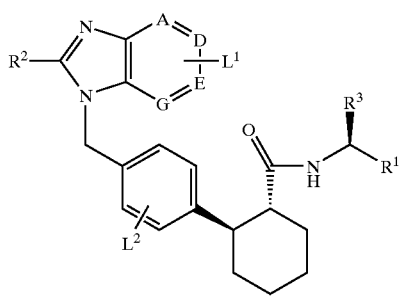
(D)

Very particular preference is given to the configuration (D).

Preference is also given to compounds of the general formula (I) in which $R^1$ represents a radical of the formula CO—$NR^4R^5$ where $R^4$ and $R^5$ have the meaning given above and the other radicals are as defined above.

Particular preference is given to compounds of the general formula (I) according to the invention
where
A, D, E and G each represent the CH group,
or one of the radicals A, D, E and G represents a nitrogen atom and the others each represent the CH group,
$L^1$ and $L^2$ are identical or different and independently of one another each represents one or more radicals selected from the group consisting of hydrogen, fluorine, chlorine, cyano, trifluoromethyl and trifluoromethoxy, $R^1$ represents the —$CH_2OH$ group, or
represents a radical of the formula —CO—$NR^4R^5$,
in which
$R^4$ and $R^5$ are identical or different and each represents hydrogen or ($C_1$–$C_3$)alky,
$R^2$ represents ($C_3$–$C_7$)-cloalkyl,
represents ($C_1$–$C_6$)alkyl which is optionally interrupted by an oxygen or sulphur atom or by a radical $NR^6$,
represents a 5- to 7-membered saturated heterocycle which is attached to the imidazole ring via a nitrogen atom and which optionally contains a further oxygen or sulphur atom, or
represents a 5- to 7-membered saturated heterocycle which contains a radical of the formula $NR^7$ and optionally additionally one nitrogen, oxygen or sulphur atom,
where ($C_3$–$C_7$)-cycloalkyl, ($C_1$–$C_6$)-alkyl which is optionally interrupted by an oxygen or sulphur atom, the 5- to 7-membered saturated heterocycle which is attached to the imidazole ring via a nitrogen atom and which optionally contains one further oxygen or sulphur atom and optionally ($C_1$–$C_6$)alkyl which is interrupted by a radical $NR^6$ and optionally the 5- to 7-membered saturated heterocycle which contains a radical of the formula $NR^7$ and optionally additionally one nitrogen, oxygen or sulphur atom are substituted by one hydroxyl group and/or by a radical of the formula —$NR^8R^9$,
in which
$R^6$ and $R^7$ are identical or different and each represents hydrogen, ($C_1$–$C_4$)alkyl, hydroxy-($C_1$–$C_4$)-alkyl or ($C_3$–$C_6$)-cycloalkyl,
$R^8$ and $R^9$ are identical or different and each represents hydrogen, ($C_1$–$C_4$) alkyl or ($C_3$–$C_6$)-cycloalkyl,
or
$R^8$ and $R^9$ together with the nitrogen atom form a 5- to 7-membered saturated heterocycle which may optionally additionally contain one oxygen or sulphur atom or a radical of the formula $NR^{10}$,
in which
$R^{10}$ represents hydrogen, ($C_1$–$C_4$)-alkyl or ($C_3$–$C_6$)-cloalkyl,
and
$R^3$ represents a phenyl, pyridyl or thienyl ring which is optionally mono- or polysubstituted by radicals selected from the group consisting of fluorine, chlorine, cyano, trifluoromethyl and trifluoromethoxy,
and to their enantiomers and diastereomers and their respective salts, hydrates and, if appropriate, their prodrugs.

Very particular preference is given to compounds of the general formula (I) where
A, D and E each represent the CH group,
G represents a nitrogen atom or represents the CH group,
$L^1$ and $L^2$ each represent hydrogen,
$R^1$ represents a radical of the formula CO—$NR^4R^5$,
in which
$R^4$ and $R^5$ each represent hydrogen,
$R^2$ represents ($C_1$–$C_4$)-alkyl which is optionally interrupted by an oxygen atom, or represents a 4-$R^7$-piperazin-1-yl radical
where ($C_1$–$C_4$)-alkyl, which is optionally interrupted by an oxygen atom, is substituted by a hydroxyl group or by a radical of the formula —$NR^8R^9$, in which R[7] represents hydrogen, $(C_1-C_4)$-alkyl or $(C_3C_6)$-cycloalkyl, R[8] and R[9] are identical or different and each represents hydrogen, $(C_1-C_4)$-alkyl or $(C_3-C_6)$-cloalkyl, or R[8] and R[9] together with the nitrogen atom form a morpholine radical, and R[3] represents a phenyl or pyridyl radical which may optionally be mono- or polysubstituted by fluorine, and to their enantiomers and diastereomers and their respective salts, hydrates and, if appropriate, their prodrugs.

Very particular preference is also given to compounds of the general formula (Ib) below

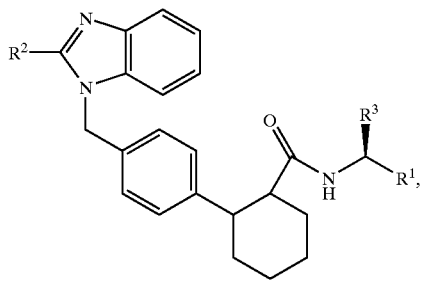
(Ib)

in which

R[1] represents a group —C(O)—NH$_2$,

R[2] represents $(C_1-C_3)$-alkyl which is substituted at the terminal C atom by a hydroxyl group, R[3] represents a phenyl ring which is optionally substituted in the para position by fluorine, or represents a pyridyl radical, and to their diastereomers and their respective salts, hydrates and, if appropriate, their prodrugs.

Very particular preference is also given to the compounds of the general formula (I) with the following structures:

(S)-N-{[(1R,2R)-2-{4-{[2-hydroxymethyl)-1H-benzimidazol-1-yl]methyl}-phenyl}-cyclohex-1-yl]carbonyl}-(4-fluorophenyl)glycinamide:

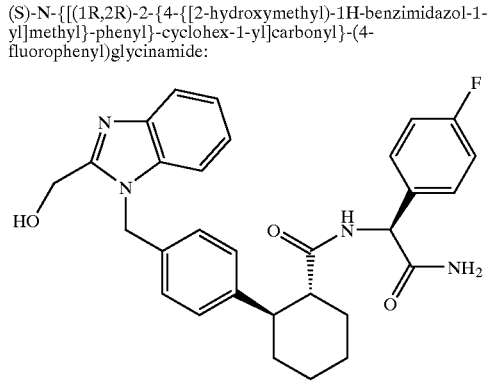

(S)-N-{[(1R,2R)-2-{4-{[2-(2-hydroxymethyl)-1H-benzimidazol-1-yl]methyl}-phenyl}-cyclohex-1-yl]carbonyl}-phenylflycinamide:

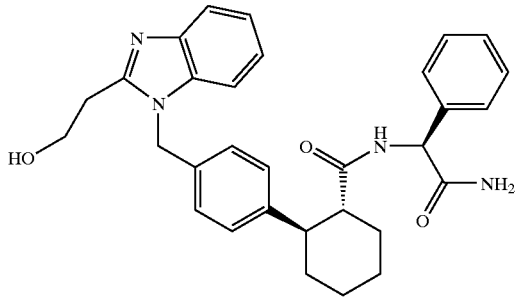

(S)-N-{[(1R,2R)-2-{4-{[2-(3-hydroxypropyl)-1H-benzimidazol-1-yl]methyl}-phenyl}-cyclohex-1-yl]carbonyl}-(3-pyridyl)glycinamide:

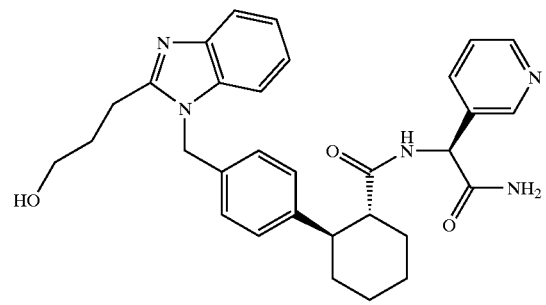

(S)-N-{{(1R,2R)-{4-{2-[2-(morpholin-4-yl-methyl)-1H-pyrido[2,3-d]imidazol-1-yl]methyl}-phenyl}-cyclohex-1-yl}carbonyl}-carbonyl}-phenylglycinamide:

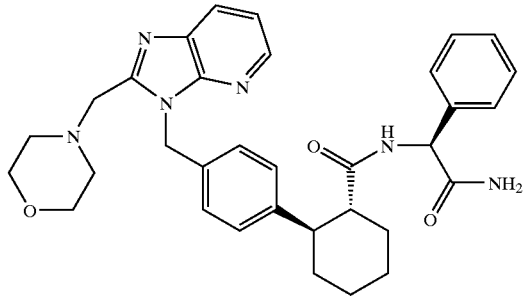

(S)-N-{[(1R,2R)-2-{4-{[2-(3-hydroxypropyl)-1H-benzimidazol-1-yl]methyl}-phenyl}-cyclohex-1-yl]carbonyl}-(4-flurophenyl)glycinamide:

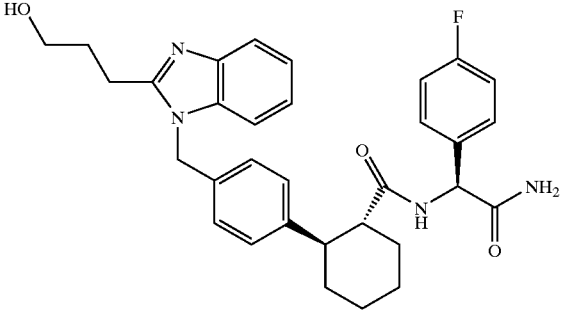

and to their salts, hydrates and, if appropriate, their prodrugs.

Among these, very particular preference is given to (S)-N-{[1R2R)-2-{4-{[2-(3-hydroxypropyl)-1H-benzimidazol-1-yl]methyl}phenyl}-cyclohex-1-yl]cabonyl}-(4-fluorophenyl)glycinamide:

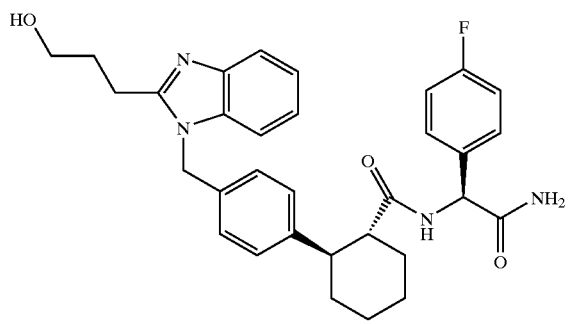

and to its salts, hydrates and, if appropriate, its prodrugs.

Moreover, processes for preparing the compounds of the general formula (I) according to the invention have been found where:

[A] compounds of the general formula (II)

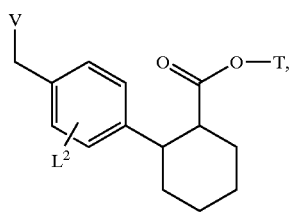

(II)

in which
L² is as defined above,
T represents (C₁–C₄)-alkyl, preferably methyl or tert-butyl, and
V represents a suitable leaving group, such as, for example, halogen, mesylate or tosylate, preferably bromine,
are initially converted by reaction with compounds of the general formula (III)

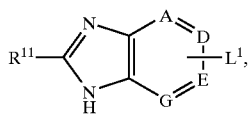

(III)

in which
A, D, E, G and L¹ are each as defined above and
R¹¹ has the meaning of R² given above, where amino and hydroxyl functions are optionally blocked by suitable amino- or hydroxyl-protective groups,
in inert solvents, depending on the definition of R¹¹ optionally in the presence of a base, into the compounds of the general formula (IV)

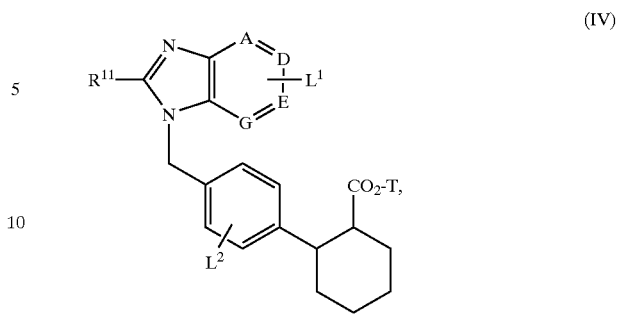

(IV)

in which
R¹¹, A, D, E, G, L¹, L² and T are each as defined above,
which are converted in a subsequent step using acids or bases into the corresponding carboxylic acids of the general formula (V)

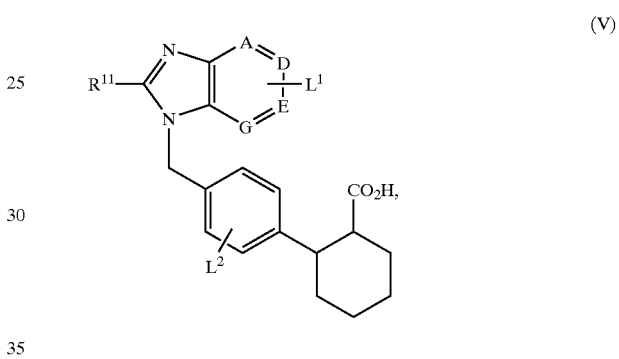

(V)

in which
R¹¹, A, D, E, G, L¹ and L² are each as defined above,
which are, if appropriate, activated, in particular by conversion into a corresponding carboxylic acid derivative, such as carbonyl halide, carboxylic anhydride or carboxylic ester,
and which are subsequently reacted by known methods with compounds of the general formula (VI) or salts thereof

(VI)

in which
R¹ and R³ are each as defined above
in inert solvents,
and, if R¹ carries one of the abovementioned protective groups, this is optionally removed by customary methods either in the hydrolysis to the acids (IV)→(V) or after reaction with the compounds of the general formula (VI), or

[B] if R² represents a saturated heterocycle which is attached directly to the imidazole ring via a nitrogen atom, the abovementioned compounds of the general formula (II) are initially converted with compounds of the general formula (IIIa)

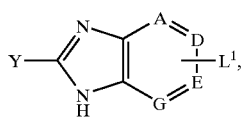
(IIIa)

in which

A, D, E, G and $L^1$ are each as defined above and

Y represents halogen or mesylate, preferably chlorine, bromine or mesylate, in inert solvents into the corresponding compounds of the formula (VI)

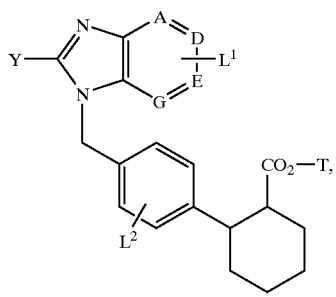
(VII)

in which

Y, A, D, E, G, $L^1$, $L^2$ and T are each as defined above, which are reacted in a subsequent step with compounds of the general formula (VII)

$$HNR^{12}R^{13} \quad \text{(VIII)},$$

in which $R^{12}$ and $R^{13}$ together with the nitrogen atom form a heterocycle according to the definition of $R^2$ to give compounds of the general formula (IX)

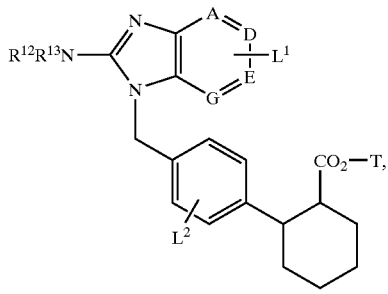
(IX)

in which

A, D, E, G, $L^1$, $L^2$, $R^{12}$, $R^{13}$ and T are each as defined above, which are, in the subsequent steps, converted as described under [A] by hydrolysis into the corresponding carboxylic acids of the general formula (X)

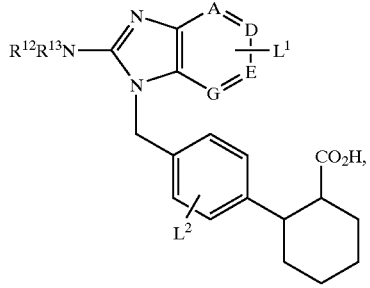
(X)

in which

A, D, E, G, $L^1$, $L^2$, $R^{12}$ and $R^{13}$ are each as defined above and these compounds are finally reacted with the compounds of the general formula (VI) according to known methods customary for preparing amides from carboxylic acids and amines (for example, if appropriate, after an activation has been carried out, in particular by conversion into a corresponding activated carboxylic acid derivative, such as carbonyl halide, carboxylic anhydride or carboxylic ester) to give the compounds of the general formula (I).

The compounds of the general formula (I) obtained according to process variant [A] or [B] can subsequently, if appropriate, be converted into the corresponding salts by reaction with, for example, an acid.

The compounds of the corresponding diastereomeric and enantiomeric forms are prepared correspondingly, either using enantiomerically or diastereomerically pure starting materials or by separating the racemates formed afterwards using customary methods (for example resolution of racemates, chromatography over chiral columns and the like).

Thus, it is possible to prepare, for example, the compounds of the preferred configuration of the general formula (Ia)

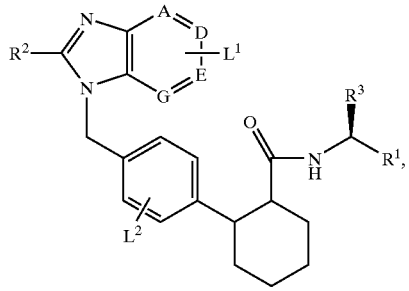
(Ia)

where the substituents $R^1$, $R^2$, $R^3$, $L^1$ and $L^2$ and the radicals A, D, E and G are as defined above by using, instead of the racemic compound of the general formula (VI), the enantiomerically pure compound of the general formula (VI a)

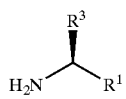
(VIa)

or salts thereof

A very particularly preferred compound of the general formula (VI a) is (S)-(4-fluorophenyl)glycinamide

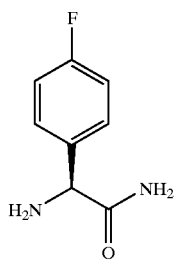
and its salts (for example the hydrochloride).
A compound of the general formula (VI a) which is likewise very particularly preferred is (S)-(3-pyridyl) glycinamide and its salts.
The processes according to the invention can be illustrated in an exemplary manner by the following formula schemes:
[A]
[B]
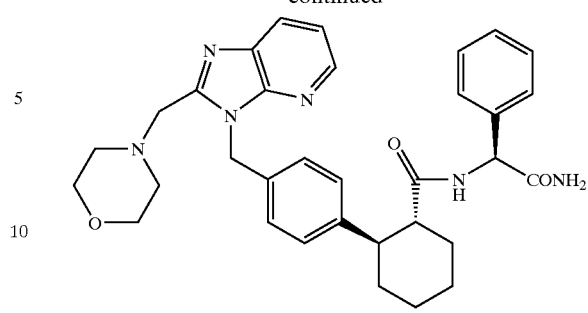
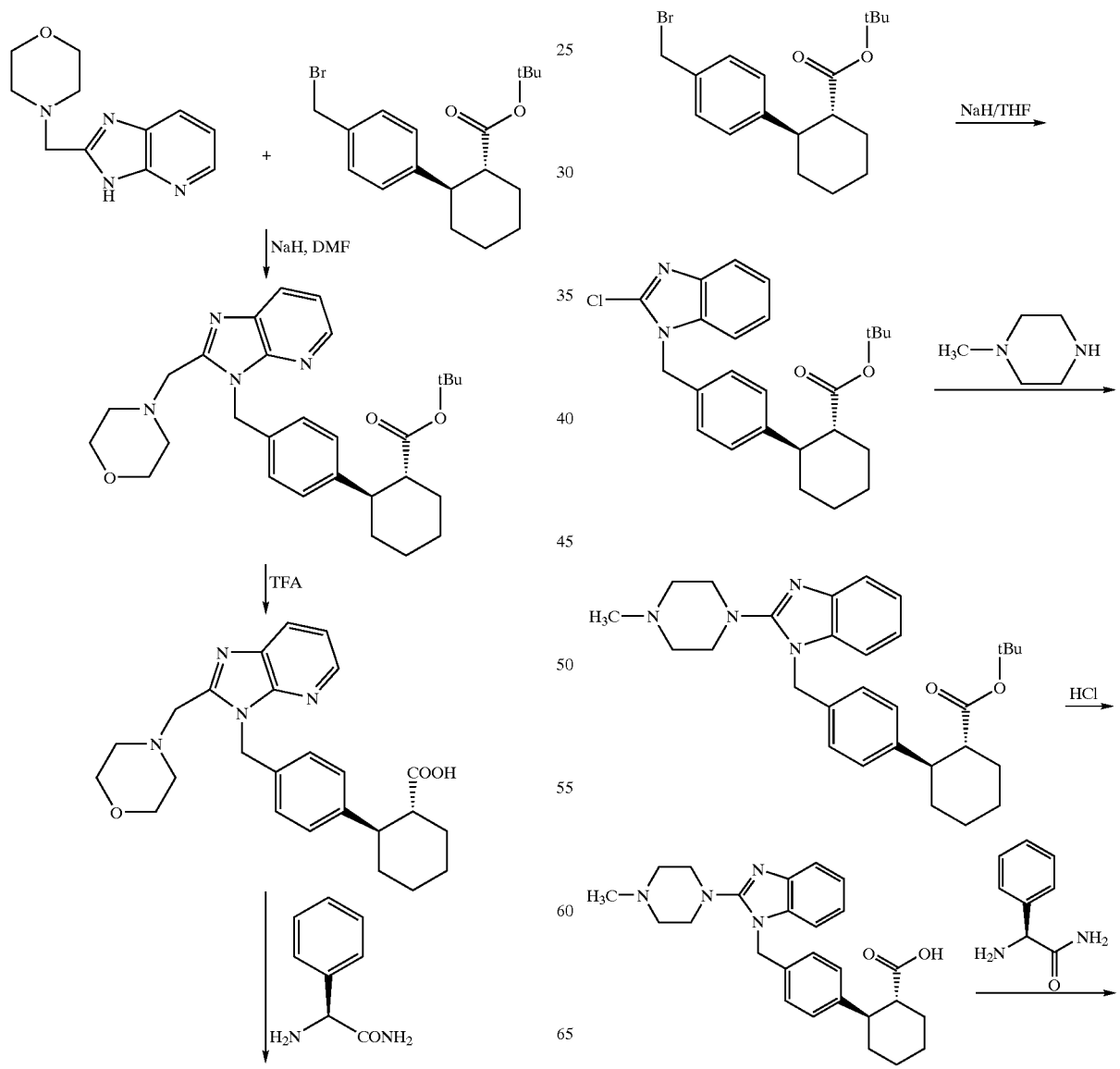

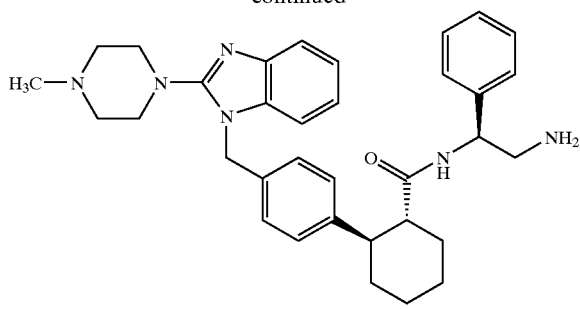

Suitable amino protective groups in the context of the invention are the customary amino protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl ethoxycarbonyl, propoxycarbonyl, isopropoxycarbonyl, butoxycarbonyl, isobutoxycarbonyl, tert-butoxycarbonyl allyl-oxycarbonyl vinyloxycarbonyl, 2-nitrobenzyloxycarbonyl, 3,4,5-trimethoxybenzyloxycarbonyl cyclohexoxycarbonyl, 1,1-dimethylethoxycarbonyl, adamantylcarbonyl, phthaloyl, 2,2,2-trichloroethoxycarbonyl 2,2,2-trichloro-tert-butoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl. A preferred protective group for primary amines is phthalimide. Preferred protective groups for secondary amines are benzyloxycarbonyl and tert-butoxycarbonyl.

The amino protective groups are removed in a manner known per se, for example under hydrogenolytic, acidic or basic conditions, preferably using acids, such as, for example, hydrochloric acid or trifluoroacetic acid, in inert solvents, such as ether, dioxane and methylene chloride.

A suitable hydroxyl protective group in the context of the definition given above is generally a protective group from the series: trimethylsilyl, triethylsilyl, triisopropylsilyl, tert-butyl-dimethylsilyl, tert-butyldiphenylsilyl, dimethylhexylsilyl trimethylsilylethoxycarbonyl, benzyl, triphenylmethyl (trityl), monomethoxytrityl (MMTr), dimethyloxytrityl (DMTr), benzyloxycarbonyl, 2-nitrobenzyl, 4-nitrobenzyl, 2-nitrobenzyloxycarbonyl, 4-nitrobenzyloxycarbonyl, tert-butyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]-methyl, 2-methylthiomethoxy) ethoxycarbonyl, tetrahydropyranyl, benzoyl, N-succinimide, 4-methylbenzoyl, 4-nitrobenzoyl, 4-fluorobenzoyl, 4-chlorobenzoyl or 4-methoxybenzoyl. Preference is given to tert-butyldimethylsilyl.

The hydroxyl-protective group is removed in a manner known per se, for example using acid or base, or by addition of tetrabutylammonium fluoride, or is carried out during the hydrolysis of the carboxylic acid.

Suitable solvents for the processes are customary organic solvents which do not change under the reaction conditions. These include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, tetrachloromethane, dichloroethylene, trichloroethylene or chlorobenzene, or ethyl acetate, pyridine, dimethyl sulphoxide, dimethylformamide, N,N'-dimethylpropyleneurea (DMPU), N-methylpyrrolidone (NMP), acetonitrile, acetone or nitromethane. It is also possible to use mixtures of the solvents mentioned. For the process [A] (II)+(III)→(IV), preference is given to diethyl ether, tetrahydrofuran and dimethylformamide. Particular preference is given to dimethylformamide.

Suitable for use as bases in the process according to the invention are, in general, inorganic or organic bases. These preferably include alkali hydroxides, such as, for example, sodium hydroxide or potassium hydroxide, alkaline earth metal hydroxides, such as, for example, barium hydroxide, alkali metal carbonates, such as sodium carbonate, potassium carbonate or caesium carbonate, alkaline earth metal carbonates, such as calcium carbonate, or alkali metal or alkaline earth metal alkoxides, such as sodium methoxide or potassium methoxide, sodium ethoxide or potassium ethoxide or potassium tert-butoxide, or organic amines (trialkyl ($C_1$–$C_6$)amines), such as triethylamine, or heterocycles, such as 1,4-diazabicyclo[2.2.2]octane (DAPCO), 1,8-diazabicyclo[5.4.0]undec-7-ene (DBU), 1,5-diazabicyclo [4.3.0]non-5-ene (DBN), pyridine, diaminopyridine, methylpiperidine or morpholine. It is also possible to use, as bases, alkali metals, such as sodium, or their hydrides, such as sodium hydride. Preference is given to sodium hydride, potassium carbonate, caesium carbonate, triethylamine, trimethylamine, pyridine, potassium tert-butoxide, DBU or DABCO. Very particularly preferred for the step [A] (II)+(III)→(IV) are sodium hydride and sodium hydroxide.

In general, the base is employed in an amount of from 0.05 mol to 10 mol, preferably from 1 mol to 2 mol based on 1 mol of the compound of the formula (II).

The process (II)+(III)→(IV) according to the invention is generally carried out in a temperature range from −20° C. to +100° C., in particular from −20° C. to +60° C., preferably from 0° C. to +60° C.

The process (II)+(III)→(IV) according to the invention is generally carried out under atmospheric pressure. However, it is also possible to carry out the process under elevated pressure or under reduced pressure (for example in a range from 05 to 5 bar).

The hydrolysis of the carboxylic esters is carried out by customary methods by treating the esters in inert solvents with customary bases, the salts which are formed initially being converted by treatment with acid into the free carboxylic acids, or, in the case of the t-butyl esters, with acid.

Suitable bases for the hydrolysis are the customary inorganic bases. These preferably include alkali metal hydroxides or alkaline earth metal hydroxides, such as, for example, sodium hydroxide, lithium hydroxide, potassium hydroxide or barium hydroxide, or alkali metal carbonates, such as sodium carbonate or potassium carbonate or sodium bicarbonate. Particular preference is given to using sodium hydroxide or lithium hydroxide.

Suitable acids are, in general, trifluoroacetic acid, sulphuric acid, hydrogen chloride, hydrogen bromide and acetic acid, or mixture thereof, if appropriate with addition of water. Preference is given to hydrogen chloride or trifluoroacetic acid in the case of the tert-butyl esters and to hydrochloric acid in the case of the methyl esters.

Solvents which are suitable for the hydrolysis are water or the organic solvents customarily used for hydrolysis. These preferably include alcohols, such as methanol, ethanol, propanol, isopropanol or butanol, or ethers, such as tetrahydrofuran or dioxane, dimethylformamide, dichloromethane or dimethyl sulphoxide. It is also possible to use mixtures of the solvents mentioned. Preference is given to water/tetrahydrofuran and, in the case of the reaction with trifluoroacetic acid, dichloromethane and, in the case of hydrogen chloride, tetrahydrofuran diethyl ether, dioxane or water.

The hydrolysis is generally carried out in a temperature range from 0° C. to +100° C.

In general, the hydrolysis is carried out at atmospheric pressure. However, it is also possible to operate under reduced pressure or under elevated pressure (for example from 0.5 to 5 bar).

When carrying out the hydrolyses, the base or the acid is generally employed in an amount of from 1 to 100 mol, preferably from 1.5 to 40 mol, based on 1 mol of the ester.

Preferred auxiliaries used for the amide formations are condensing agents. Preference is given here to using the customary condensing agents, such as carbodiimides, for example N,N'-diethyl-, N,N'-dipropyl-, N,N'diisopropyl-, N,N'-dicyclohexylcarbodiimide, N-(3-dimethylaminoisopropyl)-N'-ethylcarbodiimide hydrochloride (EDC) or carbonyl compounds, such as carbonyldiimidazole, or 1,2-oxazolium compounds, such as 2-ethyl-5-phenyl-1,2-oxazolium-3-sulphate or 2-tert-butyl-5-methyl-isoxazolium perchlorate, or acylamino compounds, such as 2-ethoxy-1-ethoxycarbonyl-1,2-dihydroquinoline, or propanephosphonic acid anhydride, or isobutyl chloroformate, or bis-(2-oxo-3-oxazolidinyl)-phosphoryl chloride or benzotriazolyloxy-tri (dimethylamino)phosphonium hexafluorophosphate, or O-(benzotriazol-1-yl) N,N,N',N'-tetramethyl-uronium hexafluorophosphate (HBTU) or O-(7-azabenzotriazol-1-yl) N,N,N',N'-tetramethyl-uronium hexafluorophosphate (HATU) and, as bases, alkali metal carbonates, for example sodium carbonate or bicarbonate or potassium carbonate or bicarbonate, or organic bases, such as trialkylamines, for example triethylamine, N-ethylmorpholine, N-methylpiperidine or diisopropylethylamine. Particular preference is given to the combination of EDC, N-methylmorpholine and 1-hydroxybenzotriazole.

The compounds of the general formulae (II), (IIIa), (VI) and (VIII) are known or can be prepared by customary methods (cf. EP-A-0 725 061, EP-A-0 725 064).

Most of the compounds of the general formula (III) are novel, and they can be prepared, in the case that $R^{11}$ does not represent a heterocycle which is attached directly via N, by reacting compounds of the general formula (XI)

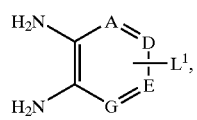
(XI)

in which
A, D, E, G and $L_1$ are each as defined above
with compounds of the general formula (XII)

$R^{11}$—$CO_2H$ (XII)

in which
$R^{11}$ is as defined above
or, if appropriate, esters, lactones or other reactive precursors thereof (for example imido esters)
if appropriate with removal of the water of reaction, if appropriate in the presence of an acid, preferably PPA, HCl and p-TsOH (cf. also J. Org. Chem. 1941, 6, 25 ff. and Bull. Soc. Chim. Fr. 1991, 128, 255–259)
and, in the case that $R^{11}$ represents one of the radicals listed above under $R^2$ which optionally also carries a protective group, by converting compounds of the general formula (XI) initially by reaction with compounds of the general formula (XIII)

HO—$R^{14}$—$CO_2H$ (XIII)

in which
$R^{14}$ represents ($C_1$–$C_8$)-alkanediyl
or, if appropriate, esters, lactones or other reactive precursors thereof (for example imido esters)
into the compounds of the general formula (XIV)

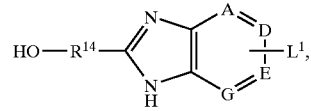
(XIV)

in which
A, B, D, G, $R^{14}$ and $L^1$ are each as defined above
in inert solvents,
subsequently substituting the hydroxyl group by halogen, mesylate or tosylate, thus producing the compounds of the general formula (XV)

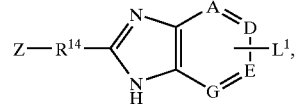
(XV)

in which
$R^{14}$, A, D, E, G and $L^1$ are each as defined above
and
Z represents halogen, mesylate or tosylate,
and reacting these with amines of the general formula (XVI)

$R^8R^9NH$ (XVI)

in which
$R^8$ and $R^9$ are each as defined above
(cf. also J. Am. Chem. Soc. 1948, 70, 3406; J. Heterocycl. Chem. 1969, 759–60).

Solvents which are suitable for the process are customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, pyridine, dimethyl sulphoxide, dimethylformamide, N,N'-dimethylpropyleneurea (DMPU), N-methylpyrrolidone (NMP), acetonitrile, acetone or nitromethane. It is also possible to use mixtures of the solvents mentioned. Preference is given to dichloromethane, tetrahydrofuran and dimethylformamide.

Bases suitable for use in the process according to the invention are, in general, inorganic or organic bases. These preferably include alkali metal hydroxides, such as, for example, sodium hydroxide or potassium hydroxide, alkaline earth metal hydroxides, such as, for example, barium hydroxide, alkali metal carbonates, such as sodium carbonate, potassium carbonate or caesium carbonate, alkaline earth metal carbonates, such as calcium carbonate, or alkali metal or alkaline earth metal alkoxides, such as sodium methoxide or potassium methoxide, sodium ethoxide or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to use, as bases, alkali metals, such as sodium, or their hydrides, such as sodium hydride. Preference is given to sodium hydride, potassium carbonate, triethylamine, trimethylamine, pyridine, potassium tert-butoxide, DBU or DABCO.

In general, the base is employed in an amount of from 0.05 mol to 10 mol, preferably from 1 mol to 2 mol, based on 1 mol of the compound of the formula (XV).

The process according to the invention is generally carried out in a temperature range of from –50° C. to +100° C., preferably from –30° C. to +60° C.

The process according to the invention is generally carried out under atmospheric pressure. However, it is also possible to carry out the process under elevated pressure or under reduced pressure (for example in a range from 0.5 to 5 bar).

The compounds of the general formulae (XII), (XII) and (XVI) are known per se or can be prepared by customary methods.

Some of the compounds of the general formulae (XV) and (XV) are novel, and they can be prepared by customary methods, for example as described above.

The compounds of the general formulae (IV), (V), (VII), (DC) and (X) and their salts are novel and can be prepared as described above.

Surprisingly, the compounds of the general formula (I) according to the invention and their analogues have an unforeseeable useful pharmacological activity spectrum, combined with an improved solubility in water, which may, if appropriate, only be achieved with the aid of formulation auxiliaries and/or by establishing a suitable pH, and, if appropriate, also combined with increased metabolic stability.

Accordingly, they can be employed for preparing medicaments for the treatment of all disorders caused by ischaemia, in particular for the acute and chronic treatment of ischaemic disorders of the cardiovascular system (such as, for example, coronary heart disease, stable and unstable angina pectoris, of peripheral and arterial occlusive diseases, of thrombotic vascular occlusions, of myocardial infarction and of reperfusion damage).

Moreover, owing to their potential to increase angiogenesis, they are particularly suitable for a permanent therapy of all occlusive diseases. The substances are therefore suitable for treating all peripheral and cardiovascular disorders caused by ischaemia, i.e. disorders of the cardiovascular system caused by ischaemia. For pharmaceutically active compounds and active compound formulations, a good solubility in water is, as is well known, an advantageous property, thus, the compounds according to the invention are, for example, particularly suitable for oral and intravenous administration.

Test systems
1. Determination of the Solubility

To determine the solubility, a precipitation method was used:

10 mg of the test substance are completely dissolved in 50 µl of DMSO (stock solution). 20 µl of this solution are added to 2000 µl of physiological saline. This solution, in turn, is shaken at 25° C. in a Thermomixer Comfort (from Eppendorf) at 1400 rpm for 24 hours for equilibration The precipitated fractions of the test substance are centrifuged off using a Biofuge 15 from Heraeus at 14,000 rpm for 5 min. 1300 µl of the supernatant are once more centrifuged using a Microfuge from Beckmann at 45,000 rpm=125,000 go 10 µl of this centrifugation supernatant are then diluted with 1000 pd of DMSO, and this solution is measured by HPLC (Hewlett Packard 1090, method, gradient from 100% PBS buffer pH=4 to 10% buffer/90% acetonitrile over a period of 15 min, column: RP18).

Using a calibration curve, the measured peak area of the HPLC measurement is converted into the substance concentration. For the calibration curve, 20 µl of the stock solution are diluted successively with DMSO such that 5 concentrations of 2.5 mg/l to 2000 mg/l result. These solutions are likewise measured by HPLC (see method above), and the peak areas are plotted as a function of the concentrations.

2. Inhibition of Adenosine Uptake in Rabbit Erythrocytes by the Compounds According to the Invention.

The capability of substances to influence the adenosine-uptake system is investigated by determining the inhibitory effect of the substances on functional adenosine uptake. For the functional adenosine-uptake test, an erythrocyte preparation from rabbit blood is used. The blood is drawn intravenously using citrate (3 ml Monovette 9NC from Sarstedt) as anticoagulant. The blood is centrifuged at 3000 g for 5 min and the erythrocytes are suspended in 10 mM MOPS/0.9% NaCl solution pH 7.4. The suspension is diluted to one hundredth of the original blood volume. In each case 990 µl of the suspension are admixed with 10 µl of a suitable concentration of the substance to be investigated, and the mixture is incubated at 30° C. for 5 min. 5 µl of a 4 mM adenosine solution are then added, and the mixture is incubated at 30° C. for another 15 min. The samples are then centrifuged at 3000 g for 5 min and in each case 700 pd of the supernatant are admixed with 28 µl of 70% strength $HClO_4$, allowed to stand in an ice bath for 30 min and centrifuged at 16,000 g for 3 min, and 350 µl of the sample are neutralized using 30 µl of 5N NaOH. 50 µl of the sample are applied to a column (Waters Symmetry C18 51 µm 3.9×150 mm). A Spherisorb ODS II 5 µm 4.6×10 mm column is used as precolumn. The mobile phase used is a gradient of 50 mM $KH_2PO^4$/5 mM tributylamine pH 7 (mobile phase A) and a mixture of mobile phase A/methanol 1/1 (mobile phase B). The gradient is from 10–40% B, at a flow rate of 0.5 ml/min. The adenosine which is present is quantified by its absorption at 260 nm, as are the hyoxanthine and inosine formed. The $IC_{50}$ is the concentration of active compound at which, 15 min after addition of adenosine, 50% of the adenosine concentration originally employed is still present.

Using this test, the $IC_{50}$ value determined for Example 3 was 15 nM, that for Example 8 was 20 nM, that for Example 10 was 25 nM and that for Example 16 was 10 nM.

3. In vivo Test Model for Testing "Adenosine-Reuptake Inhibitors"

Adult FBI (Foxhound-Beagle-Irish-Setter) dogs (20–30 kg) are initially anaesthetized using a combination of trapanal 500 mg and alloferin 55 mg. Anaesthesia is maintained by infusion of a mixture of fentanyl 0.072 mg/kg, alloferin 0.02 mg/kg and dihydrobenzpyridyl 0.25 mg/kg×min. The animals are intubated and ventilated with a mixture of $O_2/N_2O$ 1/5 using an Engström ventilation pump at 16 breaths per min and a volume of 18–24 ml/kg. The body temperature is maintained at 38° C.±0.1° C. Arterial blood pressure is measured via a catheter in the femoral artery. Thoracotomy is carried out on the left side at the fifth intercostal space. The lung is pushed back and fixed and a cut is made in the pericardium. A proximal section of the LAD distally to the first diagonal branch is exposed and a calibrated electromagnetic flow sensor (Gould Statham, model SP7515) is placed around the vessel and attached to a flow meter (Statham, model SP-2202). Distally to the flow sensor, a mechanic occluder is attached such that there are no branches in between flow sensor and occluder.

Using a catheter in the femoral vein, blood samples are taken and substances administered. A peripheral ECG is recorded using needles which are fixed subcutaneously. A microtip pressure manometer (Millar model PC-350) is pushed through the left atrium to measure the pressure in the left ventricle. Measurement of the heart frequency is triggered by the R wave of the ECG. During the entire experiment, the haemodynamic parameters and coronary flow are recorded using a multi-event recorder.

A four-minute occlusion causes reactive hyperaemia. The difference between the coronary flow under control conditions and the maximum flow during the reactive hyperaemia is measured. The time which is required to achieve half of this maximum flow in the drop is a suitable parameter to assess the reactive hyperaemia.

After a stabilization period of one hour, the experiment is started with a four-minute occlusion. Thirty minutes later, the substance is administered (i.v.) which is, after two minutes, followed by re-occlusion. The reactive hyperaemia after verum and placebo is compared.

4. Mouse Angiogenesis Model

To test the effect of adenosine-reuptake inhibitors on collateralization and neovascularization a mouse model for angiogenesis was developed. To this end, a femoral artery of the mouse is ligated at the upper end of the thigh. This induces chronic ischaemia of the hind leg in question. The other hind leg serves as individual control. To exclude residual flow through the ligated vessel, two ligatures are applied, and the vessel is cut in between. A few days after this operation, the treatment is started.

As a measurement parameter during the ongoing experiment, the temperatures of the paws of the two hind legs are measured. Owing to poorer circulation, the ischaemic hind leg has a lower absolute temperature. In each case, the temperature difference between the paws of the hind legs is calculated. This individual temperature difference is determined in different treatment groups as a function of the dose and in comparison with an untreated control. In this model, adenosine-reuptake inhibitors significantly improve the circulation of the ischaemic hind leg in comparison with the corresponding controls.

The novel active compounds can be converted in a known manner into the customary formulations, such as tablets, sugarcoated tablets, pills, granules, aerosols, syrups, emulsions, suspensions and solutions, using inert, non-toxic, pharmaceutically suitable carriers or solvents. In this connection, the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds using solvents and/or carriers, if appropriate using emulsifiers and/or dispersants, where, for example, if the diluent used is water, organic solvents can optionally be used as auxiliary solvents.

Administration is carried out in a conventional man ner, preferably orally, transdermally, parenterally, perlingually, intravenously, particularly preferably orally or intravenously.

In general, it has proven advantageous in the case of intravenous administration to administer amounts of approximately 0.0001 to 10 mg/kg, preferably approximately 0.003 to 1 mg/kg, of body weight, to achieve effective results. In the case of oral administration, 0.1 to 20 mg/kg, preferably 0.3–3 mg/kg, of body weight are employed.

In spite of this, if appropriate it may be necessary to depart from the amounts mentioned, namely depending on the body weight or on the type of administration route, on the individual response towards the medicament, the manner of its formulation and the time or interval at which administration takes place. Thus, in some cases it may be adequate to manage with less than the above-mentioned minimum amount, while in other cases the upper limit mentioned has to be exceeded. It may be advisable to divide this amount into a number of individual doses over the course of the day.

Starting materials

The following abbreviations for solvents are used in the examples:

DMF=N,N-dimethylformamide
DMSO=dimethyl sulphoxide
PPA=polyphosphoric acid
TFA=trifluoroacetic acid
THF=tetrahydrofuran

EXAMPLE 1A (1R, 2R)-2-(4-Methyl-phenyl)-cyclohexane-1-carboxylic acid

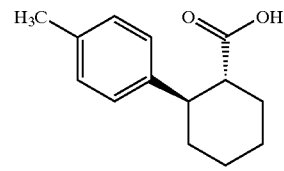

Racemic (1R*,2R*2)-(4-methyl-phenyl)-cyclohexane-1-carboxylic acid was prepared analogously to the process described in U.S. Pat. No. 5,395,840, column 16. The resulting racemic material was separated into the enantiomers using the following procedure:

The racemic acid (415 g; 1.9 mol) and triethylamine (96.2 g; 0.95 mol; 131.8 ml) were suspended in a mixture of THF (2.7 1) and water (5.3 1). At 60° C., (S)-(−)phenylethylamine (115.2 g; 0.95 mol) was added dropwise, resulting in a precipitate being formed. The mixture was stirred at 60° C. for 2 h and then cooled using an ice bath. This precipitate was filtered off with suction, giving predominantly the phenylethylamine salt of the (1S,2S)-enantiomer. The filtrate was acidified using conc. HCl and extracted twice using dichloromethane. The combined extracts were dried over sodium sulphate and concentrated. Yield: 202.4 g (28%) of a mixture of enantiomers enriched with the (1R,2R)-isomer.

This mixture was treated with R-(+)-phenylethylamine as described above to precipitate the desired enantiomer as a salt. The colourless crystals were filtered off with suction and recrystallized from acetonitrile/methanol (6:1). X-ray analysis of these crystals confirmed the (1R, 2R)-configuration. Yield 136.9 g (46%). Work-up (see above) gave 89 g of (1R, 2R)-2-(4-methylphenyl)-cyclohexane-1-carboxylic acid.

EXAMPLE 2A tert-Butyl (1R, 2R)-2-(4-bromomethyl-phenyl)-cyclohexane-1-carboxylate:

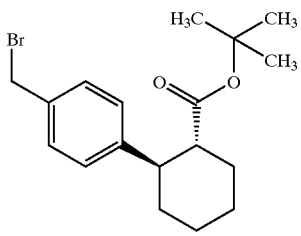

The intermediate was prepared analogously to the procedure for the racemate (U.S. Pat. No. 5,395,840, column 17). For purification, the resulting mixture was stirred with diethyl ether.

EXAMPLE 3A 2-(2-Phthalimidylethyl)-1H-benzimidazole

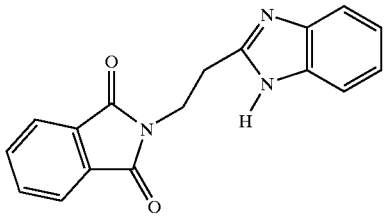

2-Aminoethylbenzimidazole dihydrochloride (*Bull. Soc. Chim. Fr.* 1991, 128, 255–259; 2.34 g, 10 mmol), phthalic anhydride (1.63 g, 11 mmol) and triethylamine (2.79 ml, 20 mmol) in chloroform (25 ml) were heated at reflux overnight, and the mixture was then cooled to room temperature, diluted with ethyl acetate and filtered off. The filtrate was washed with saturated sodium carbonate solution, buffer (pH=7) and saturated sodium chloride solution and dried over sodium sulphate. Chromatography (dichloromethane:methanol 10:1, $R_f$=0.4) gave 2.08 g of 2-(2-phthalimidylethyl)-benzimidazole (71.4% of theory) as a colourless foam. MS (DCI, $NH_3$)=292 (M+H$^+$). $^1$H-NMR (DMSO-$d_6$): 3.15 (2H, t); 4.0 (2H, t); 7.05–7.2 (2H, m); 7.4–7.5 (2H, m); 7.8–7.9 (4H, m); 12.4 (1H, br s).

The remainder of the synthesis is carried out following the general procedures A, B and C as mentioned below, and in a last step, the phthalimide group is cleaved off as described below.

EXAMPLE 4A 2-(2-Hydroxyethoxymethyl)-pyrido[2,3-d]-1H-imidazole

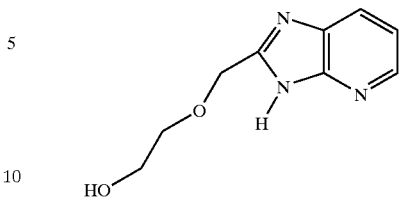

1,4-Dioxan-2-one (6.13 g, 60 mmol) and 2,3-diaminopyridine (5.46 g, 50 mmol) in mesitylene (100 ml) were heated at reflux in a Dean-Stark separator for 10 h. After cooling, mesitylene was decanted off and the residue was purified by silica gel chromatography (dichloromethane:methanol 9:1) (yield: 8.47 g, 87% of theory).
MS(DCI)=194 (M+H, 100%); $^1$H-NMR (DMSO-$d_6$): 3.78 (2H, m); 3.89 (2H, m); 4.91 (2H, s); 5.3 (1H, s); 7.18 (1H, dd); 7.95 (1H, d); 8.43 (1H, dd); 12.7 (1H, br s).

EXAMPLE 5A

2-[2-(tert-Butyldimethylsilyloxy)ethoxymethyl]-pyrido[2,3-d]-1H-imidazole

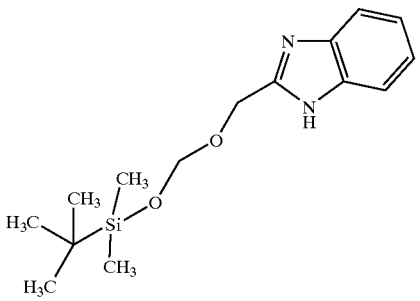

8.4 g (43.48 mmol) of 2-(2-hydroxyethoxymethyl) (pyrido-[2,3-d]-1H-imidazole) and 4.84 g (47.82 mmol) of triethylamine were dissolved in 120 ml of DMF and admixed with 7.21 g (47.8 mmol) of TBDMS chloride, the mixture warming to about 40° C. Stirring at room temperature was continued for 2 h, and the mixture was then poured into water, giving the product in crystalline form. The product was filtered off with suction, washed with a little water and dried under high vacuum. $^1$H-NMR (DMSO-$d_6$): 0.02 (6H, s); 0.83 (9H, s); 3.52 (2H, t); 3.75 (2H, t); 4.73 (2H, s); (1H, dd); 7.90 (1H, dd); 8.43 (1H, dd); 12.9 (1H br s).

EXAMPLE 6A 2-tert-Butyldimethylsilyloxymethyl-1H-benzimidazole:

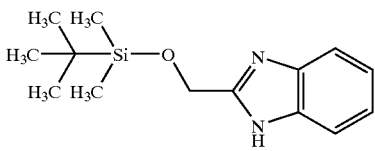

At room temperature, triethylamine (2.27 ml, 16.3 mmol) and TBDMS chloride (1.65 g, 10.95 mmol) were added to a solution of 2-hydroxymethylbenzimidazole (1.48 g, 9.95 mmol) in DMF-(30 ml). After 3.5 h, the reaction-was terminated by addition of water, the mixture was extracted with diethyl ether and the organic phase was dried over sodium sulphate. Chromatography (silica gel, cyclohexane-:ethyl acetate 2:1, $R_f$=0.35) gave 2.52 g of 2-tert-butyldimethylsilyloxymethyl-benzimidazole (97% of theory) as a brownish powder. MS (DCI, NH$_3$)=263 (M+H$^+$). $^1$H-NMR (DMSO-d$_6$): 0.00 (6H, s); 0.80 (9H, s); 4.75 (2H, s); 7.0–7.1 (2H, m); 7.4–7.5 (2H, m); 12.15 (1H, br s).

EXAMPLE 7A 2-(2-Hydroxyethoxymethyl)-1H-benzimidazole:

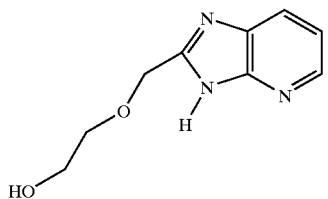

Using a Dean-Stark separator, 1,4-dioxan-2-one (2.04 g, 20 mmol) and 1/2-diaminobenzene (2.16 g, 20 mmol) were heated under reflux in mesitylene (150 ml) for 10 h. The crystals formed on cooling were then filtered off with suction (2.94 g, 77% of theory). $R_f$ (dichloromethane:methanol 10:1)=0.45, MS (EI)=192 (M+, 20%), 148 (20%), 147 (40%), 132 (100%4), $^1$H-NMR (DMSO-d$_6$): 3.6 (4H, s); 4.65 (1H, s); 4.7 (2H, s); 7.1–7.2 (2H, m); 7.45 (1H, d); 7.55 (1H, d); 12.4 (1H, br s).

EXAMPLE 8A 2-(3{[tert-Butyl(dimethyl)silyl]oxy}propyl)-1H-benzimidazole

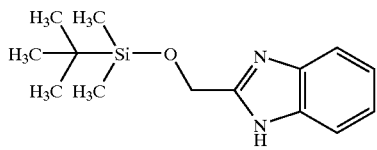

The silylation of 2-(3-hydroxypropyl)-1H-benzimidazole was carried out analogously to the process described in Example 6A.

To this end, tert-butyldimethylsilyl chloride (TBDMSCl) (14.68 g, 97.37 mmol) was added a little at a time to a solution of 2-(3-hydroxypropyl)-benzimidazole (15.60 g, 88.52 mmol) in DMF (265 ml) and triethylamine (20.27 ml, 145.41 mmol). The mixture was stirred at RT overnight and then admixed with water (800 ml) and extracted with diethyl ether. The organic phase was dried over sodium sulphate and chromatographed over silica gel (mobile phase: cyclohexane/ethyl acetate=6:1), giving 25 g (97%) of colourless crystals. MS (DCI): 291 (M+H)+

$^1$H-NMR (CDCl$_3$): 0.12 (6H, s); 0.92 (9H, s); 2.08 (2H, m); 3.10 (2H, t); 3.80 (2H, t); 7.20 (2H, m); 7.52 (2H, br. s).

EXAMPLE 9A (S)-(4-Fluorophenyl)glycinamide hydrochloride

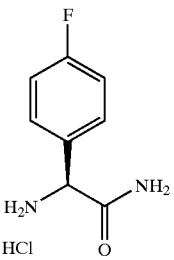

Route 1:
a) (S)-N-(tert-Butoxycarbonyl)-(4-fluorophenyl)glycine

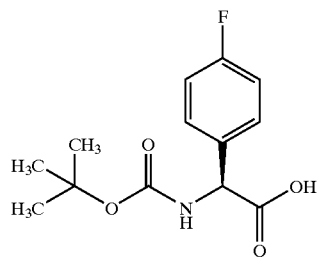

(S)-(4-Fluorophenyl)glycine (35 g, 207 mmol) and sodium carbonate (54.8 g, 517 mmol) were initially charged in water (150 ml) and tetrahydrofuran (75 ml), and di-tert-butyl pyrocarbonate (Boc anhydride) (52.3 ml, 228 mmol) was added dropwise at room temperature. The reaction mixture was stirred overnight at RT. Using 5N hydrochloric acid, the reaction solution was adjusted to pH 3 and extracted with dichloromethane and water, and the aqueous phase was re-extracted twice with dichloromethane. The combined organic phases were dried over sodium sulphate and filtered, and the solvent was removed under reduced pressure. The product (54.2 g, 97% of theory) was reacted without any further purification.

MS (ESI)=561 (2M+Na$^+$, 40%), 292 (M+Na$^+$, 100%), 236 (40%), 214 (70%), 153 (95%).

$^1$H-NMR (DMSO-d$_6$): 1.38 (9H, s); 5.11 (1H br. d); 7.12–7.21 (2H, m); 7.39–7.47 (2H, m); 7.56 (1H, br. d); 12.78 (1H, br. s).

b) (S)-N-(tert-Butoxycarbonyl)-(4-fluorophenyl) glycinamide

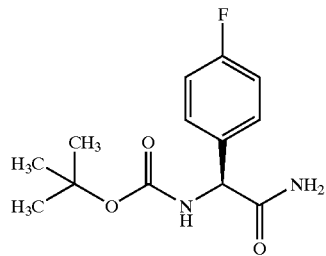

Under argon, the product from Example 9A a) (54.2 g, 201 mmol) was dissolved in tetrahydrofuran (600 ml), the mixture was cooled to −15° C. (internal temperature) and triethylamine (201 mmol, 28.1 ml) and isobutyl chloroformate (201 mmol, 26.1 ml) were added successively over a period of 5 min. The mixture was stirred at −15° C. for 25 min, after which ammonia in methanol (126 ml of a 2N solution) was added, and the reaction mixture was stirred at this temperature for 30 min. The mixture was filtered and the filter residue was dissolved in dichloromethane and extracted with water. The organic phase was washed twice with sodium carbonate solution and dried over sodium sulphate, and the solvent was removed under reduced pressure. The residue was admixed with petroleum ether and crystallized at 4° C. overnight. After filtration and rinsing with petroleum ether, the product (33.9 g, 63% of theory) was isolated as a solid.

$R_f$(methanol:dichloromethane=1:10)=0.46

MS (DCI/NH$_3$)=269 (M+H$^+$, 60%), 169 (100%).

$^1$H-NMR (DMSO-d$_6$): 137 (9H, s); 5.09 (1H, br. d); 7.1–7.3 (4H, m); 7.37–7.51 (2H, m); 7.57 (1H, br. s).

c) (S)-(4-Fluorophenyl)glycinamide hydrochloride

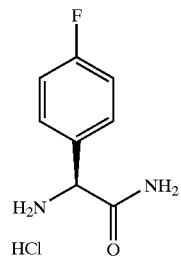

The product from Example 9A b) (33.8 g, 126 mmol) was dissolved in a solution of hydrogen chloride in 1,4-dioxane (250 ml of a 4N solution) and 1,4-dioxane (100 ml), and the mixture was stirred at RT for 2 h. The resulting precipitate was filtered off with suction, washed with diethyl ether and, after drying under reduced pressure, triturated once more with diethyl ether, filtered off with suction and dried under reduced pressure. The product was isolated as a colourless solid (24.3 g, 94.4% of theory) of an enantiomeric purity>99% ee.

MS (DCI/NH$_3$)=337 [2(M−HCl)+H$^+$, 20%], 169 [(M−HCl)+H$^+$, 100%].

$^1$H-NMR (DMSO-d$_6$): 4.97 (1H, s); 7.2–7.4 (2H, m); 7.5–7.7 (2H, m); 8.13 (1H, s); 8.80 (3H, s).

Route 2:

Alternatively to route 1, it was possible to prepare the compound from Example 9A c), i.e. (S)-(4-fluorophenyl)glycinamide hydrochloride, by the following route:

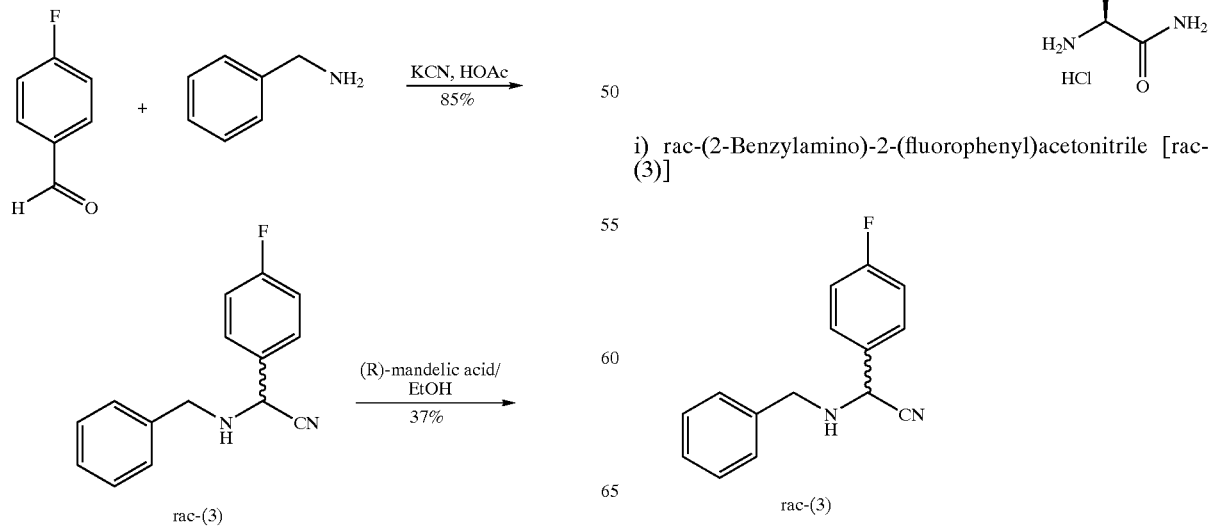

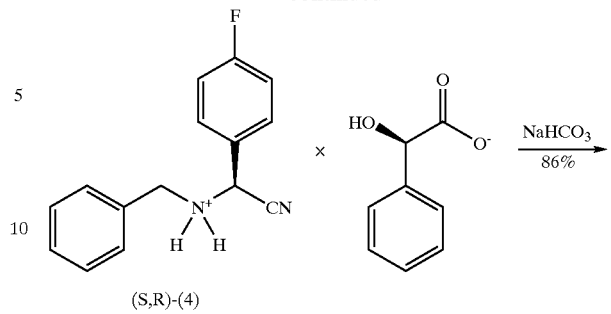

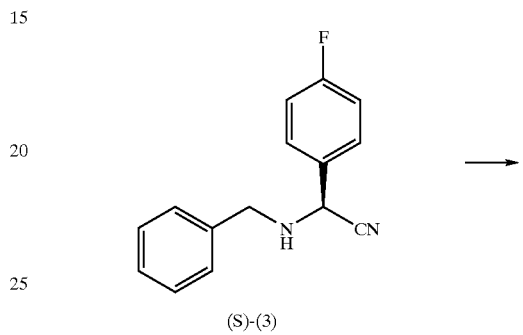

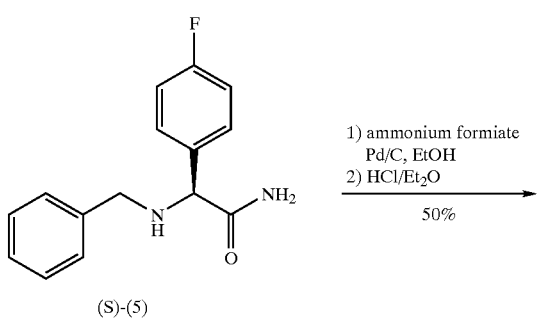

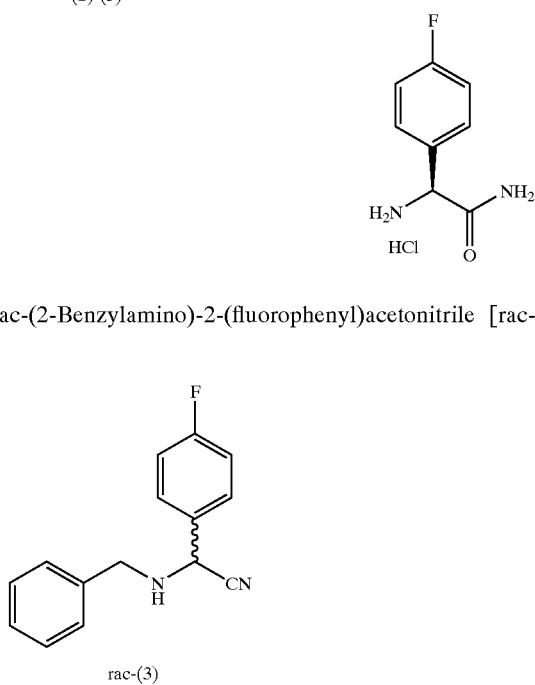

i) rac-(2-Benzylamino)-2-(fluorophenyl)acetonitrile [rac-(3)]

4-Fluorobenzaldehyde is initially reacted with benzylamine in a cyanide solution in acetic acid in a so-called Strecker reaction, which is one of the standard reactions in amino acid syntheses (see, for example, the four literature references: 1.) Hassan, N. A., Bayer, E., Jochims, J. C., *J.Chem.Soc. Perkin* 1 1998, 3747–3757; 2.) Georgiadis, M. P., Haroutounian, S. A., *Synth. Comm.* 1989, 616; 3.) Alabaster, RJ., Gibson, A. W., Johnson, S. A., Edwards, J. S., Cottrell, I. F., *Tetrahedron Asymmetry* 1997, 8, 447–450, quoted therein: Alabaster, R. J.; Cottrell, I. F.; Gibson, A. W.; Johnson, S. A.: UK Patent Appl. 9511031.8; 4.) Inaba, T., Fujita, M., Oguia, K, *J.Org.Chem.* 1991, 56, 1274–1279).

Under the conditions described in literature reference 1.) (Hassan, N. A., Bayer, E., Jochims, J. C., J.Chem.Soc. Perkin 1 1998, 3747–3757), the racemic (2-benzylamino)$_{24}$-fluorophenyl)acetonitrile [rac-(3)] was prepared in a yield of 85%.

ii) (S)-Benzyl[cyano(4-fluorophenyl)methyl]ammonium (R)-amygdalate [(S,R)-(4)]

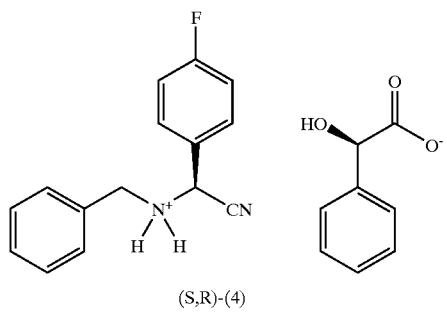

(S,R)-(4)

The racemic product from Example 9A i) was then dissolved in ethanol and admixed with (R)-mandelic acid to isolate, in a kinetic racemate separation, the diastereomerically pure (S)-benzyl[cyano(4-fluorophenyl)methyl] ammonium (R)-amygdalate (see literature reference 1.) above, *J.Chem.Soc. Perkin* 11998, 3747–3757). 63% of the diastereomerically pure product was isolated here.

iii) (2S)N-Benzyl-(4-fluorophenyl)acetonitrile [(S)-(3)]

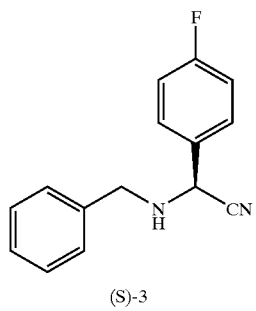

(S)-3

From the product from Example 9A ii), the enantiomerically pure (2S)-N-benzyl-(4-fluorophenyl)acetonitrile was obtained in a yield of 87% (see literature reference 1.), *J.Chem.Soc.Perkin* 1 1998, 3747–3757).

iv) (2S)-N-Benzyl-(4-fluorophenyl)glycinamide

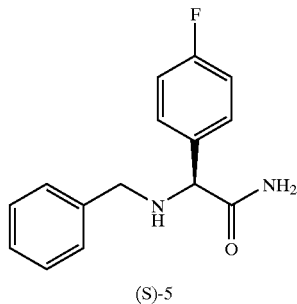

(S)-5

The enantiomerically pure (2S)-N-benzyl-(4-fluorophenyl)acetonitrile from Example 9A iii) was hydrolysed using conc. sulphuric acid to give (2S)-N-benzyl-(4-fluorophenyl)glycinamide in a yield of 97% (see literature reference 1.), *J.Chem.Soc. Perkin* 1 1998, 3747–3757).

For the conversion of rac-3) into racemic N-benzy-(4-fluorophenyl)glycinamide, an alternative method using $H_2O_2/K_2CO_3$ is described in the prior art (see literature reference 3.), Alabaster, R. J., Gibson, A. W., Johnson, S. A., Edwards, J. S., Cottrell, I. F., *Tetrahedron Asymmetry* 1997, 8, 447450, cited therein: Alabaster, R. J.; Cottrell, I. F.; Gibson, A. W.; Johnson, S. A.: UK Patent Appl. 9511031.8). (S)-(4-Fluorophenyl)glycinamide hydrochloride

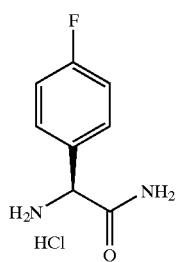

For the debenzylation, which has hitherto not been described, of the product from Example 9A iv), a solution of this product (1.5 g, i.e. 5.8 mmol of (2S)N-benzy-(4-fluorophenyl)glycinamide) in ethanol (37.5 ml) was admixed with 50% water-moist 5% palladium-on-carbon (1.5 g), ammonium formate (1.5 g, 23.8 mmol) and water (18.8 ml), and this mixture was heated to reflux temperature. After 2 h at reflux, the mixture was filtered, the palladium-on-carbon was washed with cold ethanol (two times 3 ml) and the solution was concentrated. The crude product was stirred with a little ethyl acetate, once more filtered off with suction and concentrated to dryness. The evaporation residue was admixed with 1N HCl in ether and evaporated to dryness. The colourless product was dried under reduced pressure. 0.6 g of the product (S)-4-fluorophenylglycinamide hydrochloride (50% of theory) was isolated. The MS and $^1$H-NMR-spectroscopic data corresponded to those given above in Example 9A c).

General Procedure for Alkylation [A]:

In a typical batch, sodium hydride (6.3 mmol) was, at 0° C., added to a solution of the imidazole of the general formula (III) (6 mmol) in dry DMF (30 ml). After 30 min at room temperature and 30 min at 40° C., the compound of the general formula (II) (6.3 mmol) was added at 0° C., and the reaction mixture was stirred at room temperature overnight. The reaction was then terminated by addition of water, the mixture was extracted with diethyl ether and the organic phase was then dried over sodium sulphate. Chromatography (silica gel, cyclohexane:ethyl acetate) gave the product in a yield of 60–90%.

Alternatively to the reaction of the imidazole with sodium hydride in DMF, it is also possible to carry out the reaction using sodium hydroxide in THF.

General Procedure for Ester Hydrolysis [B]:

In a typical batch, trifluoroacetic acid (5 ml) was added at room temperature to a solution of the ester of the general formula (IV) (T=tert-Bu; 1.5 mmol) in dichloromethane (5 ml). After 2 h, the mixture was cooled to 0° C., adjusted to pH=2 using aqueous sodium hydroxide solution (about 30 ml, 2 M) and extracted with dichloromethane. Drying of the organic phase over sodium sulphate gave, after concentration, the compound of the general formula (V).

General Procedure for Amide Formation [C]:

A suspension of acid (V) (4 mmol), (S)-phenylglycinamide hydrochloride (4.2 mmol), 1-hydroxybenzotriazole (4.4 mmol), EDC hydrochloride (4.8 mmol) and triethylamine (12 mmol) in dichloromethane or dimethylformamide (DMF) (40 ml) was stirred at room temperature for 24–48 h. Water was added, and the mixture was then extracted with dichloromethane (in some cases with methanol) and the organic phase was dried over sodium sulphate (or magnesium sulphate) and chromatographed (silica gel, dichloromethane: methanol). This gave the desired product in a yield of 60–80%.

Analogously to procedure C, it is possible to employ phenylglycinol instead of phenylglycinamide.

PREPARATION EXAMPLES

EXAMPLE 1

(S)-N-{(1R*, 2R*)-{4-[2-(2-Aminoethyl-benzimidazol-1-yl)methyl]phenyl}-cyclo -hex-2-yl-carbonyl}-phenylglycinamide

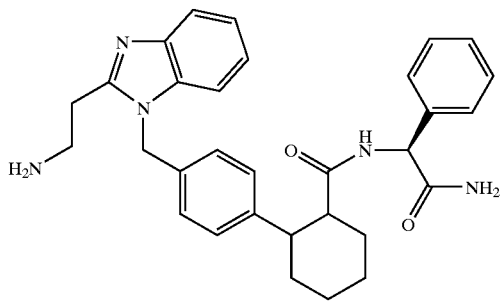

Hydrazine hydrate (0.38 ml, 7.82 mmol) was added to a suspension of (2S)-N-[(2R*)-(4-{2-(2-phthaloylaminoethyl)-benzimidazol-1-yl-methyl}-phenyl)-cyclohexyl -(1R*)-carbonyl]-phenylglycinamide (prepared according to the general procedures [A–C] from the compound of Example 3A and the racemate of Example 2A according to U.S. Pat. No. 5,395,840, Example IV; 500 mg, 0.78 mmol, mixture of diastereomers) in ethanol (25 ml). The mixture was stirred at room temperature overnight and then adjusted to pH=2 using hydrochloric acid (1 M) and concentrated. The mixture was partitioned between 10% aqueous sodium bicarbonate solution and dichloromethane and the organic phase was dried over sodium sulphate and chromatographed (silica gel, dichloromethane:methanol:conc. aqueous ammonium 100:13:1.3, $R_f$(10:1:0.2)=0.1), giving the title compound (292 mg, 72%, mixture of diastereomers) as a yellowish powder. MS(DCI, NH$_3$)=510 (M+H$^+$). $^1$H-NMR(DMSO-d$_6$): 1.2–1.5 (4H, m); 1.6–1.9 (4H, m); 2.0 (2H, br s); 2.6–3.0 (6H, m); 5.1–5.2 (A:1 H, d; B:1 H, d); 5.4–5.5 (A:2H, s; B:2H, s); 6.85–7.0 (4H, m); 7.1–7.3 (7H, m); 7.4–7.5 (1H, m); 7.55–7.65 (4H, m); 8.05–8.15 (A:1 H, d; B:1 H, d).

EXAMPLE 2

(S)-N-{(1R, 2)-{4-{[2-(2-Aminoethyl)-benzimidazol-1-yl]methyl}phenyl}cyclohex-1-yl-carbonyl}phenylglycinamide dihydrochloride

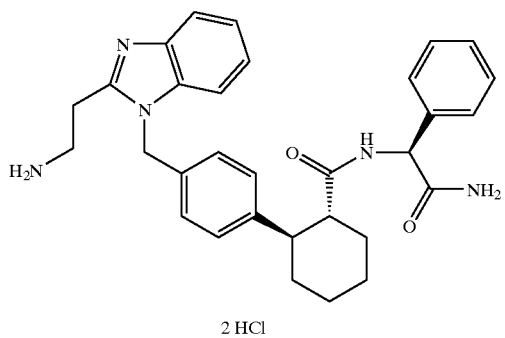

2 HCl

Chromatographic separation of the starting material from Example 1 (silica gel, methylene chloride:methanol) gave diastereomerically pure (S)-(N)-{(1R, 2R)-2-{4-{2-[2 (phthaloyl-amino)ethyl]-benzimidazol-1-yl-methyl}-phenyl}-cyclohex-1-yl-carbonyl}-phenylglycinamide which was deprotected analogously to Example 1 and then dissolved completely in as small an amount of dichloromethane as possible, treated with about two equivalents of 1M HCl in diethyl ether and concentrated.

Found: C64.21H6.58
Calc.: C63.91H 6.49

EXAMPLE 3

(S)-N-{{(1R, 2R)-{4-{2-[2-(Morpholin-4-yl-methyl)-1H-pyrido[2,3-d]-imidazol-1-yl]methyl}-phenyl}-cyclohex-1-yl}carbonyl}-phenylglycinamide

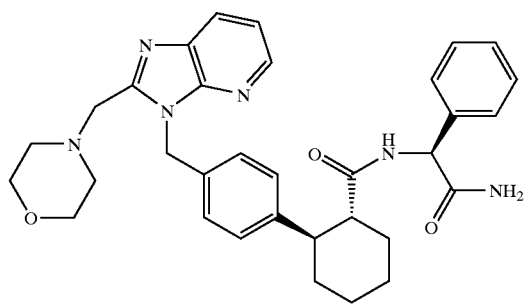

2-Hydroxymethyl-1H-pyrido[2,3-d]imidazole

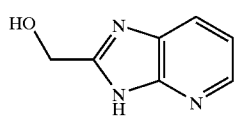

2,3-Diaminopyridine (54.6 g; 0.5 mol) and glycolic acid (38 g; 0.5 mol) in 700 ml of mesitylene were heated under reflux using a Dean-Stark separator until the calculated amount of water had separated out. The mixture was then cooled to room temperature and the resulting precipitate was filtered off with suction and boiled in 800 ml of water, with addition of activated carbon, for 15 min. The hot suspension was filtered and cooled to room temperature, and colourless crystals then precipitated out, which were filtered off with suction and dried. Yield: 56.4 g (75%).

b) 2-Choromethyl-1H-pyrido[2,3-d]imidazole hydrochloride:

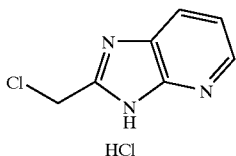

HCl

The compound from Example 3a (14.9 g; 100 mmol) was suspended in 25 ml of ethanol and a stream of dry HCl was introduced until saturation had been reached. The resulting hydrochloride was filtered off with suction and dried under reduced pressure. Yield 18.1 g (100%). The product was suspended in 100 ml of chloroform and admixed with 35 ml of thionyl chloride. The mixture was then heated under reflux for 24 h and then filtered hot, and the precipitate was washed with chloroform and dried under reduced pressure. Yield 18.9 g (92%).

c) 2-(Morpholin-4-yl-methyl)-1H-pyrido[2,3-d]imidazole:

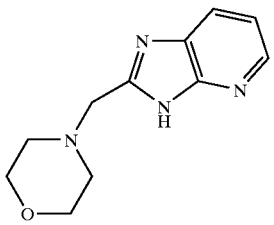

The compound from Example 3b (13.7 g; 67 mmol) and morpholine (28.6 g, 328 mmol) were heated under reflux for 3 h. The mixture was concentrated and the residue was taken up in sodium bicarbonate solution. This suspension was admixed with activated carbon and boiled for 15 min and then filtered whilst still hot. The mixture was concentrated and the resulting product was then purified by column chromatography (silica gel (70–230 mesh ASTM); mobile phase: 100:30:1 ethyl acetate/ethanol/triethylamine). The product can be recrystallized from ethyl acetate/hexane.

d) tert-Butyl (1R,2R)-{4-{[2-(morpholin-4-yl-methyl)-1H-pyrido[2,3-d]-imidazol1-yl]methyl}phenyl}-cyclohexane-1 carboxylate

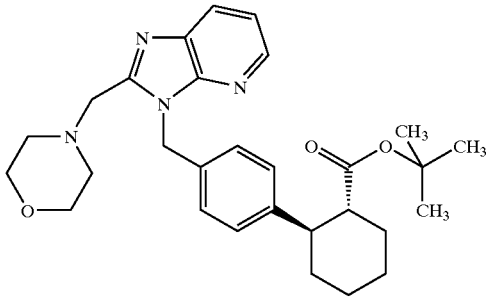

Under argon, a 60% strength suspension of sodium hydride in oil (2 g; 51.6 mmol) was suspended in 150 ml of DMF, and the compound from Example 3 c) (9.5 g, 43.5 mmol) was added. The mixture was heated at 50° C. for 30 min, resulting in the formation of a precipitate. The mixture was then cooled to room temperature and the compound from Example 2A (17.3 g; 44 mmol) was added, and the mixture was then stirred at room temperature for 20 h. The resulting clear solution was concentrated under high vacuum and the residue was taken up in dichloromethane/water. The organic phase was separated off, dried over sodium sulphate and concentrated. The residue was then purified by column chromatography (silica gel (70–230 mesh ASTM); mobile phase: 100:4 dichloromethane/methanol). Yield 10 g (47%) of a brown viscous oil.

e) (1R,2R)-2-{4-{[2-Morpholin-4-yl-methyl)-1H-pyrido[2,3-d]imidazol-1-yl]-methyl}phenyl}cyclohexane-1-carboxylic acid

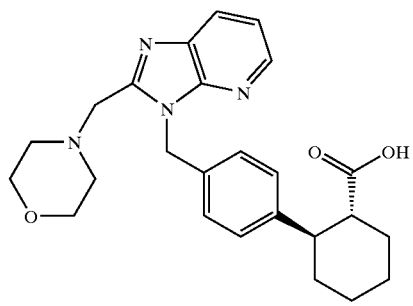

The compound from Example 3d (10 g; 20.4 mmol), 120 ml of dichloromethane and 100 ml of trifluoroacetic acid were stirred at room temperature for 1 h. With cooling, the mixture was then neutralized using concentrated aqueous sodium hydroxide solution, and the organic phase was separated off, dried and concentrated. The residue was purified by column chromatography (mobile phase: dichloromethane/methanol 100:6). Yield 7.3 g (80%) of a colourless amorphous solid.

f) (S)-N-{{(1R,2R)-2-{4-{[2-(Morpholin-4-yl-methyl)-1H-pyrido[2,3-d]imidazol-1-yl]methyl}-phenyl}-cyclohex-1-yl}carbonyl}-phenylglycinamide

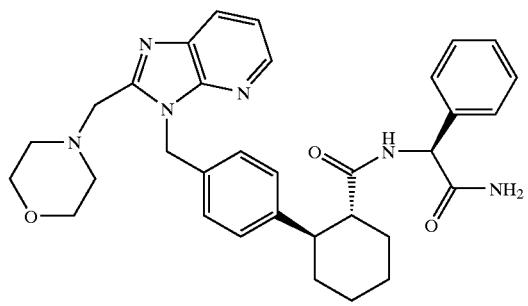

According to the general procedure [C], the compound from Example 3e (1.4 g; 3.22 mmol) was reacted with addition of a spatula tip of DMAP (4-dimethylaminopyridine). For work-up, the product was extracted with dichloromethane and purified by column chromatography (dichloromethane/methanol 100:6). Yield 1.7 g (93%) of a pale yellowish powder.

$^1$H-NMR (300 MHz; CDCl$_3$) δ[ppm]: 1.25–1.5 (3H; br m), 1.62 (1H; dq), 1.8 (3H; m), 1.94 (1H; dd), 2.31 (1H; dt), 2.42 (4H, br m), 2.67 (1H; dt), 3.61 (6H; m), 5.21 (1H; d), 5.49 (1H, br s), 5.63 (2H; d+d), 5.72 (1H; br s), 6.41 (1H; d), 6.82 (2H; d), 6.92 (2H; d), 6.98 (2H; d), 7.13 (2H; t), 7.18 (1H; t), 7.23 (1H; dd), 8.03 (1H; d), 8.42 (1H; d)

MS (DCI/NH$_3$)[m/e]: 567 (100, M+H)

EXAMPLE 4

(S)-N-{{(1R, 2R)-{4-{2-[2-(Morpholin-4-yl-methyl)-1H-pyrido[2,3-d]imidazol-1-yl]methyl}-phenyl}cyclohex-1-yl}carbonyl}-phenylglycinamide hydrochloride The compound from Example 3 was dissolved completely in as small an amount of dichloromethane as possible and treated with approximately 2 equivalents of 1M HCl in diethyl ether. The resulting precipitate was filtered off with suction [m.p. 158° C. (decomp.)].

EXAMPLE 5

(S)-N-{{(1R, 2R)-2-{4-{[2-(4-Methyl-piperazin-1-yl)-benzimidazol-1-yl]methyl}-phenyl}-cyclohex-1-yl}carbonyl}-phenylglycinamide a) tert-Butyl (1R, 2R)-2-{4-[(2-chloro-benzimidazol-1-yl)methyl]-phenyl}-cyclohexane-1-carboxylate

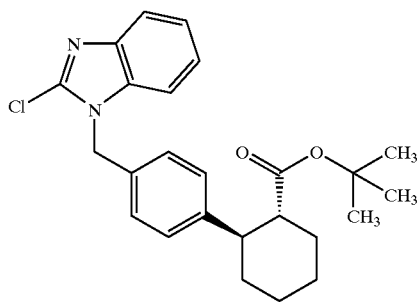

The title compound was prepared according to the general procedure [A] from 2-chlorobenzimidazole and the compound from Example 2A [$R_f$-(cyclohexane:ethyl acetate=1:1)=0.85].

b) (1R,2R)-2-{4-{[2-(4-Methyl-piperazin-1-yl)-benzimidazol-1-yl]methyl}-phenyl}-cyclohexane-1-carboxylic acid

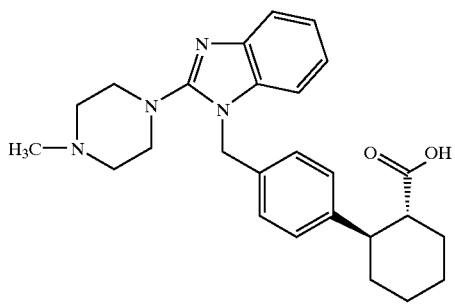

A solution of the compound from Example 5a (34.0 g, 56.0 mmol) in N-methylpiperazine (77.7 ml, 700 mmol) was heated at 100° C. overnight and then concentrated and chromatographed (silica gel, dichloromethane:methanol= 20:1 to 10:1, $R_f$(10:1)=0.32). This gave 32.0 g of tert-butyl (1R, 2R)-2-{4-{[2-(4-methyl-piperazin-1-yl)benzimidazol-1-yl]methyl}-phenyl}-cyclohexane-1 carboxylate which were reacted at room temperature with hydrochloric acid (180 ml, 6 M) overnight. The reaction mixture was washed at pH=7 with dichloromethane and the organic phase was dried over magnesium sulphate and chromatographed (silica gel, dichloromethane:methanol 5:1, $R_f$=0.13), giving 19 g (78% of theory over 2 steps) of the title compound. MS(ESI)=433 (M+H$^+$). $^1$H-NMR(DMSO-d$_6$): 1.35–1.5 (4H, m); 1.65–1.8 (3H, m); 1.9–2.0 (1H, m); 2.2 (3H, s); 2.42.5 (5H, m); 2.6–2.7 (1H, m); 3.15 (4H, Ψ t); 3.4 (1H, very br s); 5.2 (2H, s); 7.0–7.2 (7H, m); 7.4 (1H, d).

c) (S)-N-{{(1R,2R)-2-{4-{[2-(4-Methyl-piperazin-1-yl)-benzimidazol-1-yl]methyl}-phenyl}-cyclohex-1-yl}-carbonyl}-phenylglycinamide

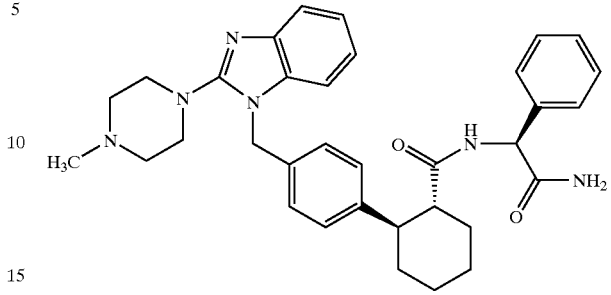

A suspension of the compound from Example 5b (19 g, 43.9 mmol), (S)-phenylglycinamide hydrochloride (8.61 g, 46.1 mmol), 1-hydroxybenzotriazol (7.68 g, 48.3 mmol), EDC hydrochloride (9.68 g, 50.5 mmol) and triethylamine (24.5 ml, 175.7 mmol) in dichloromethane (1000 ml) was stirred at room temperature over the weekend. After addition of water, the mixture was extracted with dichloromethane/methanol and the extract was dried over magnesium sulphate and concentrated. The slightly yellowish solid was stirred with dichloromethane/methanol (10:1, 220 ml) and the pure title compound was filtered off and dried under reduced pressure at 40° C. (14.5 g, 59%). $R_f$ (dichloromethane:methanol 10:1)=0.30. MS(DCI, NH$_3$)= 565 (M+H$^+$). $^1$H-NMR(DMSO-d$_6$): 1.2–1.5 (4 H, m); 1.6–1.85 (4 H, m); 2.2 (3 H, s); 2.45 (4H, Ψ t); 2.65 (1 H, br t); 2.8 (H, td); 3.15 (4 H, Ψ t); 5.15 (1 H, d); 5.2 (2 H s); 6.9 (2 H, d); 6.95–7.2 (11 H, m); 7.45 (1 H, d); 7.6 (1 H, br s); 8.0 (1 H, d).

EXAMPLE 6

(S)-N-{{(1R, 2R)-2-{4-{[2-{(4-Methyl-piperazin-1-yl)-benzimidazol-1-yl]methyl}-phenyl}-cyclohex-1-yl}carbonyl}-phenylglycinamide hydrochloride

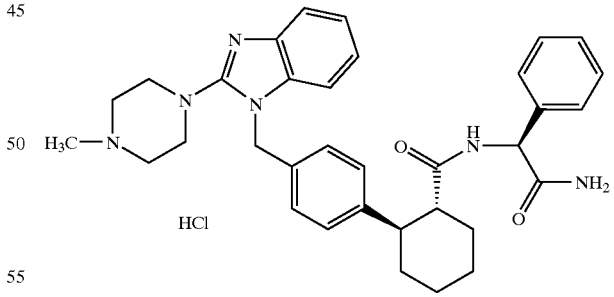

The compound from Example 5 (100 mg, 0.177 mmol) was dissolved in dichloromethane/methanol (2.5:1; 5 ml) and admixed with 1M HCl/diethyl ether (0.177 mmol), and the mixture was stirred for 5 min and then concentrated cold under reduced pressure. The title compound was obtained as a colourless powder (106 mg). M.p. 200° C. (decomp.).

The Examples 7 to 10 listed in Table 1 below were prepared analogously to Example 5 using the appropriately substituted piperazines.

TABLE 1

| Ex. No. | Structure | $R_f$* |
|---|---|---|
| 7 | 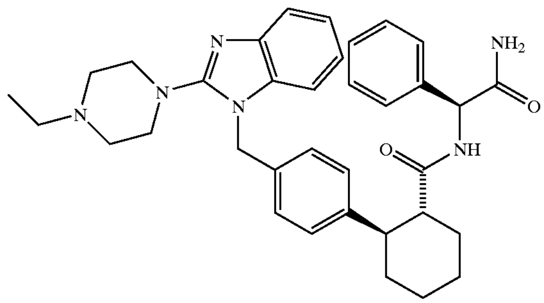 | 0.3 (10:1:0) |
| 8 | 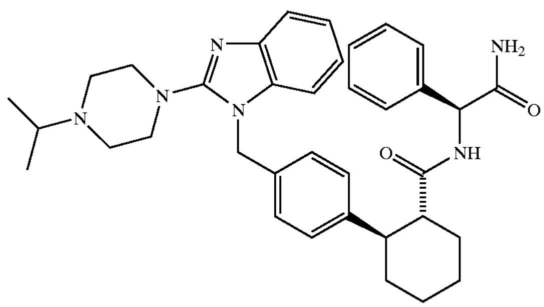 | 0.3 (10:1:0.1) |
| 9 | 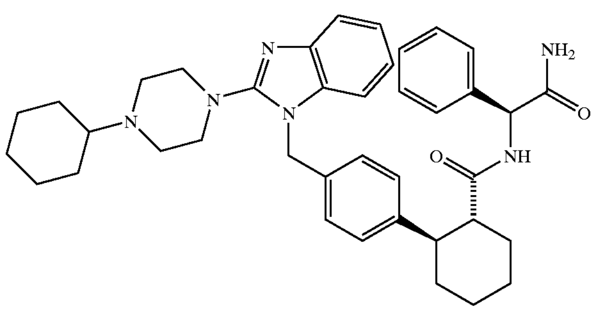 | 0.4 (10:1:0.1) |
| 10 | 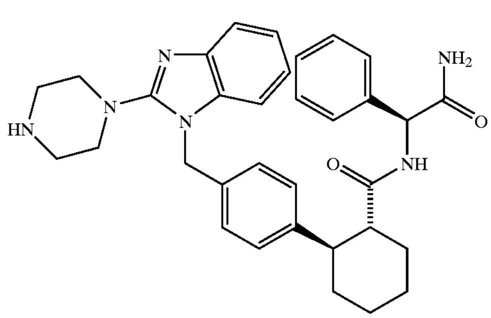 | 0.3 (10:1:0.1) |

*CH$_2$Cl$_2$:methanol:conc. ammonia

The Examples 11 and 12 listed in Table 2 below are prepared starting with the compound from Example 6A, according to the general procedures A, B and C.

TABLE 2

| Ex. No. | Structure | $R_f$* |
|---|---|---|
| 11 | 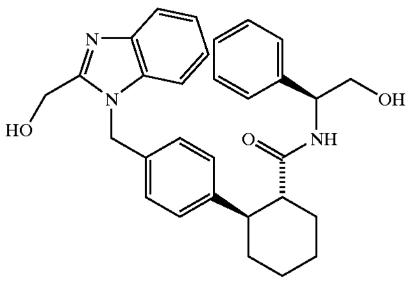 | 0.4 (10:1) |
| 12 | 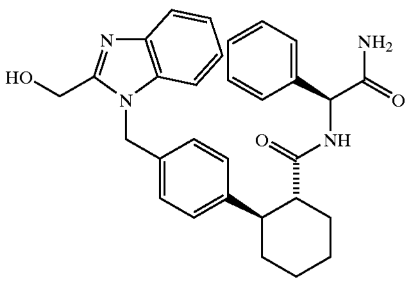 | 0.35 (10:1) |

*$CH_2Cl_2$:methanol

EXAMPLE 13

(S)-N-55 -55 (1R, 2R)-2-{4-{[2-(2-Hydroxyethoxy)methyl]-benzimidazol-1-yl}methyl}-phenyl}-cyclohex-1-yl)carbonyl}-phenylglycinamide

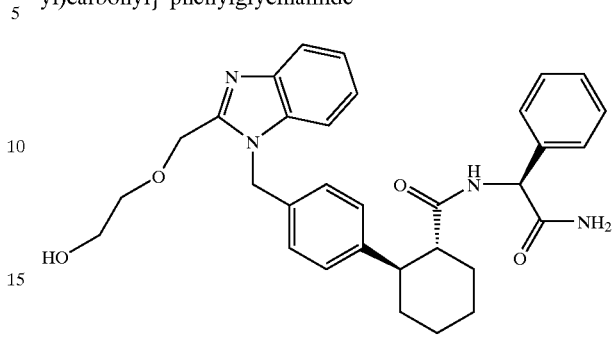

The title compound is obtained starting with the compound of Example 7A, which is silylated analogously to Example 6A using TBDMS chloride and then reacted according to the general procedures A, B and C.

$R_f$(dichloromethane:methanol 20:1)=0.20.

MS(ESI)=541 (M+H$^+$). $^1$H-NMR(DMSO-$d_6$): 1.2–1.5 (4H, m); 1.6–1.9 (4H, m); 2.6–2.7 (1H, m); 2.75–2.85 (1H, m); 3.5 (4H, s); 4.65 (1H, br s); 4.6 (2H, s); 5.15 (1H, d); 5.55 (2H, s); 6.9 (2H, d); 6.95–7.2 (10H, m); 7.45 (1H, m); 7.6 (1H, s); 7.65 (1 H, m); 8.05 (1H, d).

The Examples 14 to 16 listed in Table 3 below are prepared analogously to Example 13 from the appropriate starting materials.

TABLE 3

| Ex. No. | Structure | $R_f$ ($CH_2Cl_2$:MeOH:conc. ammonia) MS |
|---|---|---|
| 14 | 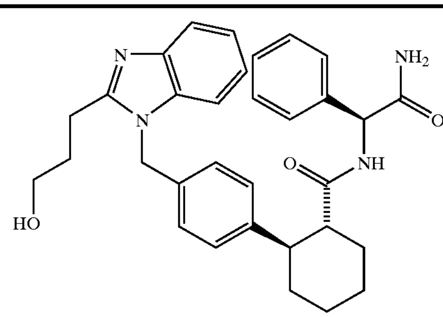 | 0.44 (10:1:0) |
| 15 | 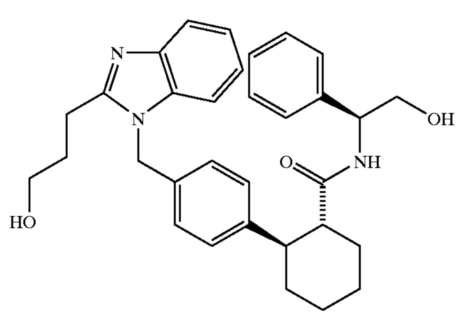 | 0.46 (10:1:0) |

TABLE 3-continued

| Ex. No. | Structure | $R_f$ (CH$_2$Cl$_2$:MeOH:conc. ammonia) | MS |
|---|---|---|---|
| 16 | 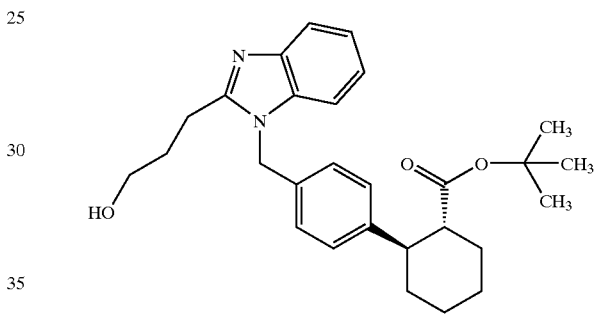 | | EI: 541 (M+) |

EXAMPLE 17

(S)-N-{[(1R,2R)-2-{4-{[2-(3-Hydroxypropyl)-1H-benzimidazol-1-yl]methyl}phenyl}-cyclohex-1-yl]carbonyl}-(4-fluorophenyl)glycinamide:

a) tert-Butyl (1R,2R)-2-(4-{[2-(3-{[tert-butyl(dimethyl)silyl]oxy}propyl)-1H-benzimidazol-1-yl]methyl}phenyl)cyclohexane-1-carboxylate:

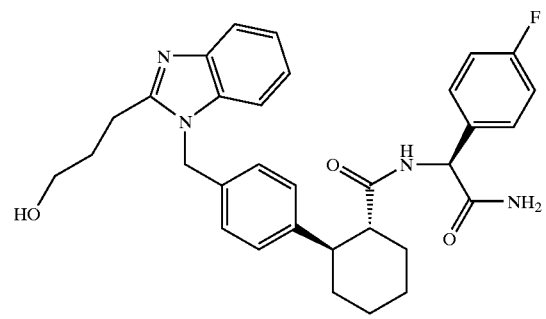

The 2-(3-{[tert-butyl(dimethyl)silyl]oxy}propyl)-1H-benzimidazole from Example 8A (22.01 g, 75.77 mmol) was added in portions to a suspension of NaH (60% in mineral oil, 3.03 g, 75.77 mmol) in DMF (480 ml). After 15 min at RT, the mixture was heated to 40° C., and stirring was continued for 30 min. After cooling to RT, the compound from Example 2A (25.5 g, 72.17 mmol) was added a little at a time, and the mixture was stirred overnight 50 ml of water were added, the mixture was extracted with diethyl ether and the organic phase was dried over sodium sulphate and chromatographed over silica gel (mobile phase: cyclohexane/ethyl acetate=10:1 to 5:1), giving 38.86 g (95.7%) of a colourless solid. MS (ESI): 563.3 (M+H)+

$^1$H-NMR (DMSO-d$_6$): 0.00 (3H, s); 0.01 (3H, s); 0.85 (9H, s); 0.99 (9H, s); 1.3–2.0 (10H, m); 2.3–2.6 (2H, m); 2.87 (2H, t); 3.69 (2H, t); 5.41 (2H, s); 6.95–7.18 (6H, m); 7.38–7.59 (2H, m)

b) tert-Butyl (1R,2R)-2-(4-{[2-(2-hydroxypropyl)-1H-benzimidazol-1-yl]-methyl}phenyl)cyclohexane-1-carboxylate:

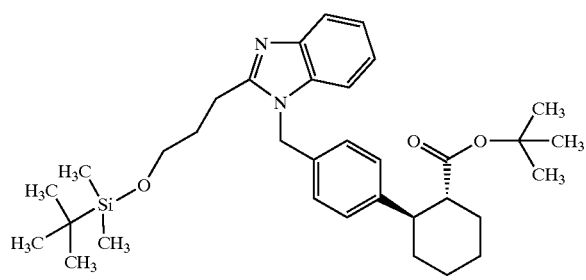

I)

A solution of tetrabutylammonium fluoride (TBAF) in THF (1.1M, 68.9 ml, 75.83 mmol) was added dropwise to a solution of the compound from Example 17a (38.80 g, 68.93 mmol) in THF (750 ml), and the mixture was stirred at RT for 30 min. The mixture was extracted with diethyl ether and the organic phase was dried over sodium sulphate and chromatographed over silica gel (mobile phase: dichloromethane/methanol=95:5), giving 29.0 g (93.8%) of a colourless solid.

MS (EST): 449.5 (M+H)+

$^1$H-NMR (DMSO-d$_6$): 0.99 (9H, s); 1.25–1.55 (4H, m); 1.6–1.8 (3H, m); 1.8–2.0 (3H, m); 2.3–2.65 (2H, m); 2.86 (2H, t); 3.49 (2H, q); 4.60 (1H, t); 5.42 (2H, s); 6.99 (2H, m); 7.08–7.18 (4H, m); 7.33–7.44 (1H, m); 7.5–7.6 (1H, m).

II.)

The compound of Example 17b) can also be prepared by coupling 2-(3-hydroxypropyl)-1H-benzimidazole directly to the compound from Example 2A, analogously to the general procedure for alkylation A.

To this end, a 60% suspension of sodium hydride in mineral oil (880 mg, 22 mmol) was initially charged in DMF (10 ml), 2-(3-hydroxypropyl)-1H-benzimidazole (3.52 g, 20 mmol), dissolved in DMF (50 ml), was added, the mixture was stirred at RT for 10 min and then heated at 40° C. for 30 min. After cooling to RT, the compound from Example 2A (7.07 g, 20 mmol), dissolved in DMF (50 ml), was added, and the reaction mixture was stirred at RT overnight. For work-up, the mixture was shaken with water and ethyl acetate, the aqueous phase was re-extracted twice with ethyl acetate and the combined organic phases were washed once with saturated sodium chloride solution. After drying over sodium sulphate, the solvent was removed under reduced pressure and the residue was crystallized by stirring with diethyl ether/petroleum ether (5:1, 70 ml). The crystalline compound was filtered off and washed with petroleum ether. Drying under reduced pressure gave 6.62 g (74% of theory) of a colourless solid which, according to spectroscopic characterization, is identical to the compound of Example 17b) I.).

c) (1R,2R)-2-(4-{[2-(3-Hydroxypropyl)-1H-benzimidazol-1-yl]methyl}phenyl)-cyclohexane-1 carboxylic acid

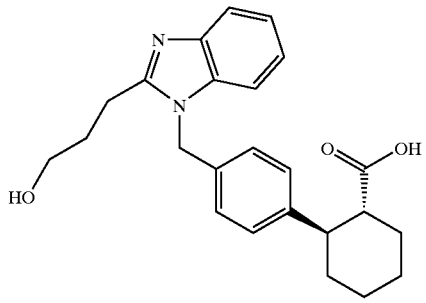

Trifluoroacetic acid (212 ml) was added to an ice-cooled solution of the compound from Example 17b) (26.5 g, 59.07 mmol) in dichloromethane (530 ml), and the mixture was slowly warmed to room temperature and stirred at room temperature overnight. The reaction mixture was then made alkaline using 1N aqueous NaOH and washed with diethyl ether. The aqueous phase was adjusted to pH 3–4 using 2N HCl (white turbidity) and extracted with methylene chloride. The organic phase was dried over sodium sulphate and the residue (white foam, 22.1 g, 95.3%) was then dried under oil pump vacuum and reacted directly, without further purification.

MS (ESI): 393.1 (M+H)$^+$ $^1$H-NMR (MeOH-d$_4$): 1.35–1.62 (4H, m); 1.75–1.90 (3H, m); 1.95–2.08 (3H, m); 2,52–2,60 (1H, m); 2,71–2,79 (1H, m); 3.25 (2H, t); 3.65 (2H, t); 5.67 (2H, s), 7.15 (2H, d); 7.24 (2H, d); 7.46–7.55 (2H, m); 7.67 (1H, d); 7.75 (1H, d).

d) (S)-N-{[(1R,2R)-2-{4-{[2-(3-Hydroxypropyl)-1H-benzimidazol-1-yl]methyl}-phenyl}-cyclohex-1-yl]carbonyl}-(4-fluorophenyl)glycinamide

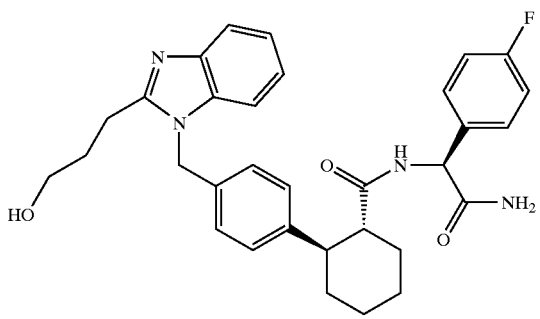

1-Hydroxybenzotriazole (6.95 g, 51.4 mmol) and N-(3-dimethylaminopropyl)-N'-ethylcarbodiimide hydrochloride (EDC×HCl) (11.68 g, 60.95 mmol) were added to a solution of the compound from Example 17c) (20.8 g, 53 mmol) in DMF (600 ml), and the mixture was stirred at room temperature for 10 min.

N-methylmorpholine (29.14 ml, 265 mmol), (S)(4-fluorophenyl)glycinamide hydrochloride (see Example 9A c) and v)) (10.85 g, 53 mmol) and a spatula tip of dimethylaminopyridine (DMAP) were then added, and the mixture was stirred at room temperature overnight. After addition of water (1.8 l), the mixture was stirred at room temperature for 2 h and then with ice-cooling for 1 h. The title compound, (S)-N-{[(1R,2R)-2-{4-{[2-(3-hydroxypropyl)-1H-benzimidazol-1-yl]methyl}phenyl}-cyclohex-1-yl]carbonyl}-(4-fluorophenyl)glycinamide, was then filtered off and washed with water, n-hexane and diethyl ether.

Drying (3 days, 100 mbar, 45° C.) gave 25.5 g (85.7%) of a colourless solid.

MS (ESI): 543 (M+H)$^+$ $^1$H-NMR (DMSO-d$_4$): 1.15–1.55 (4H, m); 1.55–2.0 (6H, m); 2.55–2.92 (4H, m); 3.48 (2H, q); 4.59 (1H, t); 5.15 (1H, d); 5.41 (2H, s); 6.856.98 (6H, m); 7.05–7.17 (5H, m); 7.35–7.42 (1H, m); 7.53–7.66 (2H, m); 8.10 (1H, d).

Instead of the (S)-(4-fluorophenyl)glycinamide hydrochloride, for example from Example 9A c) or v), it is possible to employ the free amine for the synthesis of the acid amide in question, with the same results.

EXAMPLE 18

(S)-N-{[(1R,2R)-2-{4-{[2-(hydroxymethyl)-1H-benzimidazol-1-yl]methyl}-phenyl}-cyclohex-1-yl]carbonyl}-(4-fluorophenyl)glycinamide:

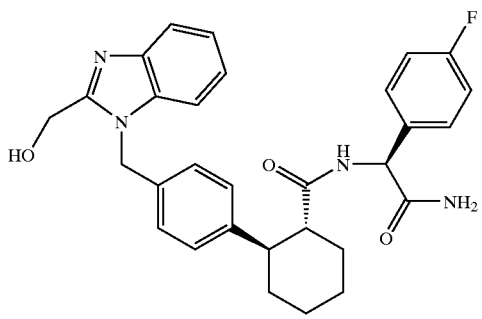

Starting with the compounds of Examples 2A, 6A and 9A c) or v), the title compound was prepared analogously to the process described in Example 17. Instead of removing the protective groups in two steps, the tert-butyldimethylsilyl ether and the tert-butyl ester of the intermediate analogous to Example 17 a) were removed in one step by action of concentrated hydrochloric acid.

R$_f$(dichloromethane/methanol=10:1): 0.38

MS (ESI):515 (M+H)$^+$ $^1$H-NMR (DMSO-d$_4$): 1.20–1.50 (4H, m); 1.61–1.78 (3H, m); 1.78–1.86 (1H, br. d); 2.65 (1H, br. t); 2.80 (1H, br. t); 4.71 (2H, br. d); 5.15 (1H, d); 5.48 (1H, d; AB-System); 5.53 (1H, d); 5.72 (1H, t); 6.87–6.94 (4H, m); 7.03–7.09 (2H, m); 7.09–7.19 (5H, m); 7.37 (1H, m); 7.58–7.65 (2H; m); 8.09 (1H, d).

EXAMPLE 19

(S)-N-{[(1R,2R)-2-{4-{[2-(2-hydroxyethyl)-1H-benzimidazol-1-yl]methyl}-phenyl}-cyclohex-1-yl]carbonyl}-phenylglycinamide

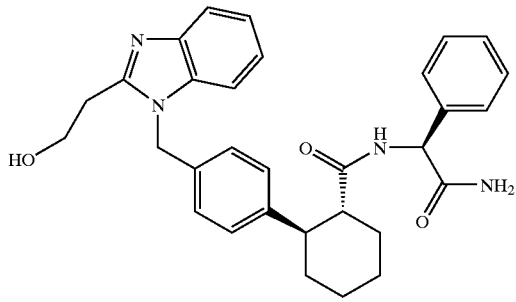

Starting from 2(2-hydroxyethyl)-1H-benzimidazole, which was prepared by standard processes, the title compound was prepared analogously to the process described for Example 17, using (S)phenylglycinamide hydrochloride instead of Example 9A c) or v).

$R_f$(dichloromethane/methanol=10:1): 0.27

MS (ESI): 511 (M+H)$^+$ $^1$H-NMR (DMSO-d$_4$): 1.15–1.52 (4H, m); 1.59–1.91 (4H, m); 2.67 (1H, br. t); 2.83 (1H, br. t); 2.98 (2H, t); 3.86 (2H; br. q); 4.89 (1H, br. t); 5.17 (1H, d); 5.44 (2H, br. s); 6.83–7.22 (12H, m); 7.38–7.48 (1H, m); 7.54–7.67 (2H, m); 8.10 (1H, d).

EXAMPLE 20

(S)-N-{[(1R,2R)-2-{4-{[(2-Hydroxyethyl)-1H-benzimidazol-1-yl]methyl}-phenyl}-cyclohex-1-yl]carbonyl}-(4-fluorophenyl)glycinamide:

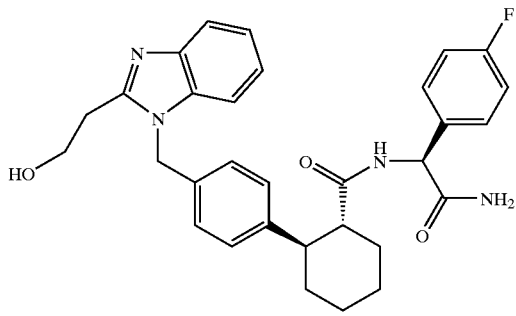

The title compound was prepared analogously to Example 19, using (S)-(4-fluorophenyl)glycinamide hydrochloride from Example 9A c) or v).

$R_f$(dichloromethane/methanol 10:1): 0.26

MS (ESI): 529 (M+H)$^+$ $^1$H-NMR (DMSO-d$_6$): 1.19–1.51 (4H, m); 1.61–1.78 (3H, m); 1.78–1.87 (1H, br. d); 2.65 (1H, br. t); 2.80 (1H, br. t); 2.97 (2H, t); 3.85 (2H, q); 4.85 (1H, t); 5.15 (1H, d); 5.44 (2H, br. s); 6.85–6.99 (6H, m); 7.08–7.19 (5H, m); 7.40 (1H, pseudo-d); 7.57 (1H, pseudo-d); 7.61 (1H, br. s); 8.10 (1H, d).

EXAMPLE 21

(S)-N-{[(1R,2R)-2-{4-{[2-(3-Hydroxypropyl)-1H-benzimidazol-1-yl]methyl}-phenyl}-cyclohex-1-yl]carbonyl}-(3-pyridyl)glycinamide:

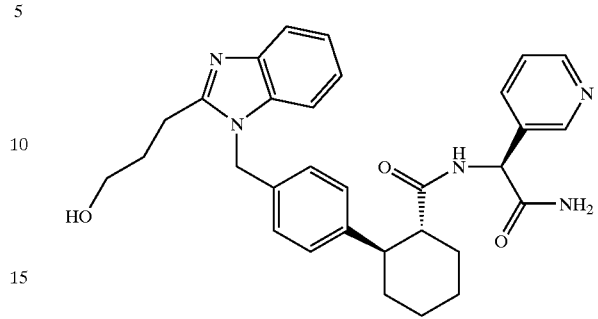

N-methylmorpholine (0.13 mL 1.2 mmol) was added to a solution of the substance from Example 17 c) (118 mg, 0.3 mmol), 1-hydroxybenzotriazole (40.5 mg, 0.3 mmol), EDC hydrochloride (69 mg, 0.36 mmol) and 4(N,N-dimethylamino) pyridine (DMAP, 1 mg) in DMF (3 ml), and the resulting mixture was transferred into a reaction vessel containing (S)(3-pyridyl)glycinamide hydrochloride (101 mg, 0.45 mg)—which can be prepared analogously to the substance from Example 9A c) or v). The reaction mixture was reacted at room temperature for three days and then purified directly by preparative high-pressure chromatography on reversed-phase silica gel (Grom-Sil 120 ODS-4 HE 5 μm) using water/acetonitrile (gradient: 10:90 to 90:10). The resulting solution was freed of acetonitrile under reduced pressure, frozen in a dry-ice bath and freeze-dried overnight. This gave 143 mg (91% of theory) of a colourless lyophilisate.

$R_f$(dichloromethane/methanol=10:1): 0.11

MS(ESI): 526 (M+H)

$^1$H-NMR (DMSO-d$_6$): 1.15–1.55 (4 H, m); 1.57–1.91 (4 H, m); 1.97 (2 H, quint.); 2.65 (1 H, br. t); 2.81 (1 H, br. t); 3.27 (2 H, t); 3.52 (2 H, t); 5.29 (1 H, d); 5.69 (2 H, s); 7.07–7.20 (4 H, m); 7.20–729 (1 H, m); 7.32 (1 H, br. s); 7.38–7.45 (1 H, m); 7.46–7.60 (2 H, m); 7.72–7.87 (3 H; m); 8.09 (1 H, br. s); 8.36 (1 h, d); 8.44 (1 H, m).

What is claimed is:
1. A compound of the formula (I)

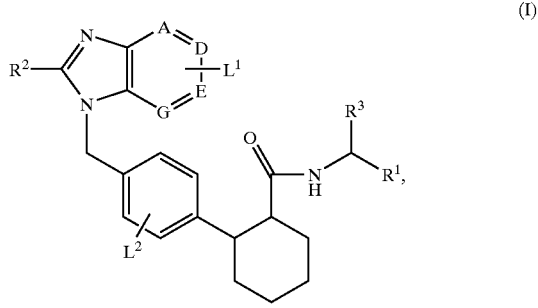

in which
A, D, E and G each represents CH,
L$^1$ and L$^2$ are identical or different and independently of one another each represents one or more radicals selected from the group consisting of hydrogen, halogen, hydroxyl, carboxyl, cyano, nitro, trifluoromethyl, trifluoromethoxy, (C$_1$–C$_6$)-alkyl, (C$_1$–C$_6$)-alkoxy and (C$_1$–C$_6$)-alkoxycarbonyl,

47

$R^1$ represents a radical of the formula CO—$NR^4R^5$,
  in which
  $R^4$ and $R^5$ are identical or different and each represents hydrogen or ($C_6$–$C_6$)-alkyl,
$R^2$ represents

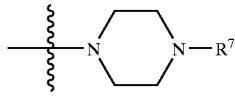

in which $R^7$ represents hydrogen, ($C_1$–$C_6$)-alkyl, hydroxy-($C_1$–$C_6$)-alkyl or ($C_3$–$C_7$)-cycloalkyl and the piperazinyl group is optionally substituted by one to three hydroxyl groups and/or by a radical of the formula —$NR^8R^9$
  in which
  $R^8$ and $R^9$ are identical or different and each represents hydrogen, ($C_1$–$C_6$)-alkyl, or ($C_3$–$C_7$)-cycloalkyl,
and
$R^3$ represents a phenyl or naphthyl group where the rings are optionally mono- or polysubstituted by at least one radical selected from the group consisting of halogen, hydroxyl, carboxyl, cyano, nitro, trifluoromethyl, trifluoromethoxy, ($C_1$–$C_6$)-alkyl, ($C_1$–$C_6$)-alkoxy and ($C_1$–$C_6$)-alkoxycarboxyl,
or an enantiomer diastereomer, salt, hydrate or prodrug thereof.

2. The compound according to claim 1
where
A, D, E and G each represents the CH group,
$L_1$ and $L_2$ are identical or different and independently of one another each represents one or more radicals selected from the group consisting of hydrogen, fluorine, chlorine, cyano, trifluoromethyl and trifluoromethoxy,
$R^1$ represents a radical of the formula HO—$NR^4R^5$,
  in which
  $R^4$ and $R^5$ are identical or different and each represents hydrogen or ($C_1$–$C_3$)-alkyl,
$R^2$ represents

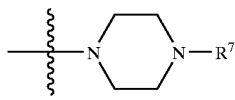

in which $R^7$ represents hydrogen, ($C_1$–$C_4$)-alkyl, hydroxy-($C_1$–$C_4$)-alkyl or ($C_3$–$C_6$)-cycloalkyl and the piperazinyl group is optionally substituted by one hydroxyl group and/or by a radical of the formula —$NR^8R^9$,
  in which
  $R^8$ and $R^9$ are identical or different and each represents hydrogen, ($C_1$–$C_4$)-alkyl or ($C_3$–$C_6$)-cycloalkyl,
and
$R^3$ represents a phenyl group which is optionally mono or polysubstituted by at least one radical selected from the group consisting of fluorine, chlorine, cyano, trifluoromethyl and trifluoromethoxy,
or an enantiomer, diastereomer, salt, hydrate or prodrug thereof.

48

3. The compound according to claim 1 or 2
where
A, D and E each represent the CH group,
G represents the CH group,
$L^1$ and $L^2$ each represent hydrogen,
$R^1$ represents a radical of the formula —CO—$NR^4R^5$,
  in which
  $R^4$ and $R^5$ each represent hydrogen,
$R^2$ represents a 4-$R^7$-piperazin-1-yl radical,
  in which
  $R^7$ represents hydrogen, ($C_1$–$C_4$)-alkyl or ($C_3$–$C_6$)-cycloalkyl,
and
$R^3$ represents a phenyl radical which may optionally be mono- or polysubstituted by fluorine,
or an enantiomer, diastereomer, salt, hydrate or prodrug thereof.

4. The compound according to claim 1
where
the radical $R^1$ represents a radical of the formula CO—$NR^4R^5$ where $R^4$ and $R^5$ are hydrogen
and
the other radicals are as defined in claim 1.

5. Compounds according to claim 1, characterized by the following stereochemistry according to formula (Ia):

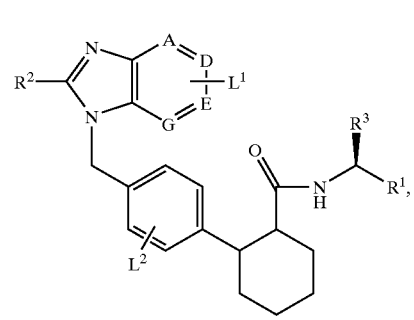

(Ia)

where the substituents $R^1$, $R^2$, $R^3$, $L^1$ and $L^2$ and the radicals A, D, E and G are each as defined in claim 1.

6. A process for preparing compounds of the formula (I) according to claim 1, characterized in that
(A) a compound of the general formula (II)

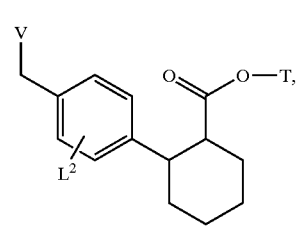

(II)

in which
$L^2$ is as defined above in claim 1,
T represents ($C_1$–$C_4$)-alkyl,
and
V represents a suitable leaving group,
is initially converted by reaction with a compound of the general formula (III)

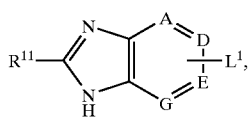
(III)

in which

A, D, E, G, and $L^1$ are each as defined above in claim 1
and $R^{11}$ has the meaning of $R^2$ given above in claim 1, where amino and hydroxyl functions are optionally blocked by suitable amino- or hydroxyl-protective groups, in an inert solvent, depending on the definition of $R^{11}$ optionally in the presence of a base, into the a compound of the general formula (IV)

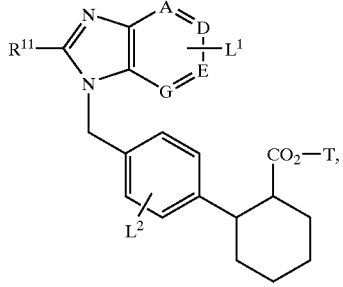
(IV)

in which $R^{11}$, A, D, E, G, $L^1$, $L^2$ are each as defined above in claim 1 and T is as defined above, which is converted in a subsequent step using acid or base into the corresponding carboxylic acid of the general formula (V)

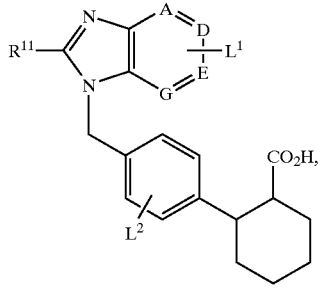
(V)

in which $R^{11}$, A, D, E, G, $L^1$, $L^2$ are each as defined above in claim 1, which is, if appropriate, activated, by conversion into a corresponding carboxylic acid derivative, and which is subsequently reacted with a compound of the general formula (VI) or salt thereof

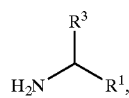
(VI)

in which $R^1$ and $R^3$ are each as defined above in claim 1 in an inert solvent, and, if $R^{11}$ carries one of the abovementioned protective groups, this is optionally removed by customary methods either in the hydrolysis to the acids (IV)→(V) or after the reaction with the compounds of the general formula (VI), or (B) if $R^2$ represents a saturated heterocycle which is attached directly to the imidazole ring via a nitrogen atom, the above mentioned compound of the general formula (II) is initially converted with a compound of the general formula (IIIa)

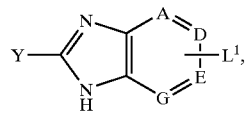
(IIIa)

in which

A, D, E, G and $L^1$ are each as defined above in claim 1
and

Y represents halogen or mesylate, in an inert solvent into the corresponding compound of the formula (VII)

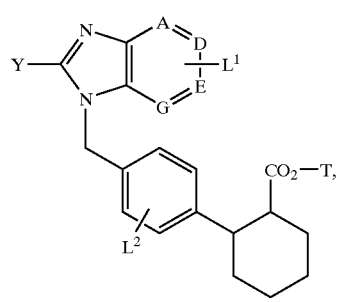
(VII)

in which

Y, A, D, E, G, $L^1$, $L^2$ are each as defined above in claim 1 and T is as defined above, which is reacted in a subsequent step with a compound of the general formula (VIII)

$HNR^{12}R^3$ (VIII)

in which $R^{12}$ and $R^{13}$ together with the nitrogen atom form a heterocycle according to the definition of $R^2$ given in claim 1 to give a compound of the general formula (IX)

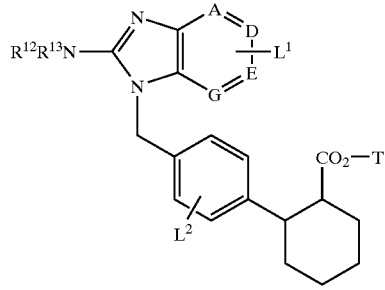

(IX)

in which

A, D, E, G, L$^1$, and L$^2$, are each as defined above in claim 1 and R$^{12}$, R$^{13}$ and T are as defined above, which is in the subsequent steps, converted as described under (A) by hydrolysis into the corresponding carboxylic acid of the general formula (X)

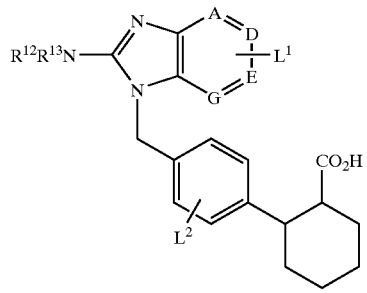

(X)

in which

A, D, E, G, L$^1$, and L$^2$, are each as defined above in claim 1 and R$^{12}$ and R$^{13}$ are as defined above and this compound is finally reacted with the a compound of the general formula (VI) according to known methods for preparing amides from carboxylic acids and amines and converted into the compound of the general formula (I)

where the compound of the general formula (I) obtained according to process variant (A) or (B) can, if appropriate, subsequently be converted into the corresponding salts.

7. A pharmaceutical composition comprising a compound of the formula (I) according to claim 1 in admixture with at least one pharmaceutically acceptable, essentially non-toxic carrier or excipient.

8. Compounds according to claim 2 where the radical R$^1$ represents a radical of the formula CO—NR$^4$R$^5$ where R$^4$ and R$^5$ are hydrogen and the other radicals are as defined in claim 2.

9. Compounds according to claim 2, with the following stereochemistry according to formula (Ia):

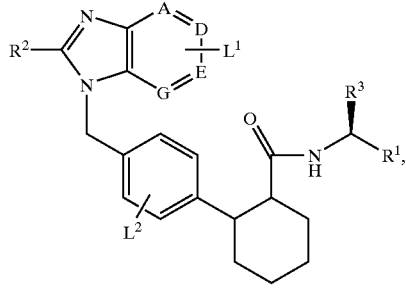

(Ia)

where the substituents R$^1$, R$^2$, R$^3$, L$^1$ and L$^2$ and the radicals A, D, E and G are each as defined in claim 2.

10. Compounds according to claim 3, with the following stereochemistry according to formula (Ia):

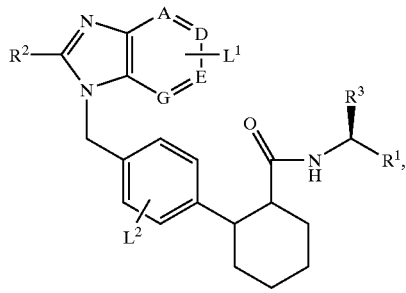

(Ia)

where the substituents R$^1$, R$^2$, R$^3$, L$^1$ and L$^2$ and the radicals A, D, E and G are each as defined in claim 3.

11. Compounds according to claim 4, with the following stereochemistry according to formula (Ia):

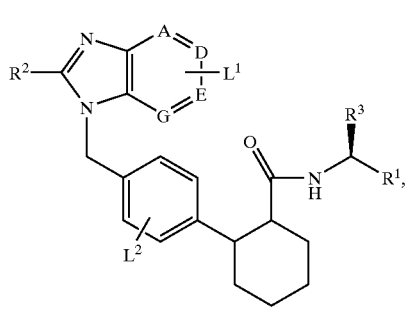

(Ia)

where the substituents R$^1$, R$^2$, R$^3$, L$^1$ and L$^2$ and the radicals A, D, E and G are each as defined in claim 4.

12. The process of claim 6 wherein T represents methyl or tert-butyl.

13. The process of claim 6 wherein V represents halogen, mesylate, or tosylate.

14. The process of claim 13 wherein V represents bromine.

15. The process of claim 6 wherein said carboxylic acid derivative of a compound of formula V is a carbonyl halide, carboxylic anhydride or carboxylic ester.

16. The process of claim 6 wherein Y of formula IIIa is chlorine or bromine.

17. The process of claim 6 wherein the steps of converting the compounds of general formula I into the corresponding salts, as provided in the final paragraph of claim 6, is carried out by reaction with an acid.

18. A pharmaceutical composition comprising a compound of the formula (I) according to claim 2 in admixture with at least one pharmaceutically acceptable, essentially non-toxic carrier or excipient.

19. A pharmaceutical composition comprising a compound of the formula (I) according to claim 3 in admixture with at least one pharmaceutically acceptable, essentially non-toxic carrier or excipient.

20. A pharmaceutical composition comprising a compound of the formula (I) according to claim 4 in admixture with at least one pharmaceutically acceptable, essentially non-toxic carrier or excipient.

21. A pharmaceutical composition comprising a compound of the formula (I) according to claim 5 in admixture with at least one pharmaceutically acceptable, essentially non-toxic carrier or excipient.

* * * * *